US012753439B2

(12) United States Patent
Kaminsky et al.

(10) Patent No.: US 12,753,439 B2
(45) **Date of Patent: *Oct. 6, 2026**

(54) DNA METHYLATION BIOMARKERS OF POST-PARTUM DEPRESSION RISK

(71) Applicants: THE JOHNS HOPKINS UNIVERSITY, Baltimore, MD (US); UNIVERSITY OF MARYLAND, Baltimore, MD (US)

(72) Inventors: Zachary Kaminsky, Ottawa (CA); Jennifer L. Payne, Baltimore, MD (US); Todd Gould, Baltimore, MD (US)

(73) Assignees: The Johns Hopkins University, Baltimore, MD (US); University of Maryland, Baltimore, MD (US)

( * ) Notice: Subject to any disclaimer, the term of this patent is extended or adjusted under 35 U.S.C. 154(b) by 939 days.

This patent is subject to a terminal disclaimer.

(21) Appl. No.: 16/990,572

(22) Filed: Aug. 11, 2020

(65) Prior Publication Data

US 2022/0049304 A1 Feb. 17, 2022
US 2023/0151423 A9 May 18, 2023

Related U.S. Application Data

(63) Continuation of application No. 14/439,468, filed as application No. PCT/US2013/068241 on Nov. 4, 2013, now Pat. No. 10,865,446.

(60) Provisional application No. 61/773,257, filed on Mar. 6, 2013, provisional application No. 61/721,660, filed on Nov. 2, 2012.

(51) Int. Cl.
*C12Q 1/68* (2018.01)
*C12Q 1/6883* (2018.01)
*G16H 50/30* (2018.01)

(52) U.S. Cl.
CPC .......... *C12Q 1/6883* (2013.01); *G16H 50/30* (2018.01); *C12Q 2600/118* (2013.01); *C12Q 2600/154* (2013.01); *C12Q 2600/158* (2013.01); *C12Q 2600/16* (2013.01)

(58) Field of Classification Search
None
See application file for complete search history.

(56) References Cited

U.S. PATENT DOCUMENTS

| | | | |
|---|---|---|---|
| 2009/0264306 A1 | 10/2009 | Caldwell et al. |
| 2011/0237537 A1 | 9/2011 | Lombard |
| 2012/0157324 A1 | 6/2012 | Lizardi et al. |

FOREIGN PATENT DOCUMENTS

| | | | |
|---|---|---|---|
| WO | 2002002809 A2 | 1/2002 |
| WO | 2004045369 A2 | 6/2004 |
| WO | 2005001131 A2 | 1/2005 |
| WO | 2008066769 A2 | 6/2008 |
| WO | 2008124428 A1 | 10/2008 |

OTHER PUBLICATIONS

Lax et al.; Frontiers in behavioral Neuroscience, vol. 16, Mar. 2022, pp. 1-5.*
Epperson, C. Neill; Am. Fam. Physician. vol. 59, pp. 2247-2254, 1999.*
Huang, et al., Estradiol acutely suppresses inhibition in the hippocampus through a sex-specific endocannabinoid and mGluR-dependent mechanism. Neuron. Jun. 7, 2012;74(5):801-8.
Forty, et al., Familiality of postpartum depression in unipolar disorder: results of a family study. Am J Psychiatry. Sep. 2006;163(9):1549-53.
Mahon, et al., Genome-wide linkage and follow-up association study of postpartum mood symptoms. Am J Psychiatry. Nov. 2009;166(11):1229-37.
Barton, et al., Dose-response characteristics of uterine responses in rats exposed to estrogen agonists. Regul Toxicol Pharmacol. Oct. 1998;28(2):133-49.
Swedenborg, et al., Regulation of estrogen receptor beta activity and implications in health and disease. Cell Mol Life Sci. Dec. 2009;66(24):3873-94.
Perrone-Bizzozero, et al., Role of HuD and other RNA-binding proteins in neural development and plasticity. J Neurosci Res. Apr. 15, 2002;68(2):121-6.
Nicolas, et al., The Jak/STAT pathway is involved in synaptic plasticity. Neuron. Jan. 26, 2012;73(2):374-90.
Bauer, et al., The neuropoietic cytokine family in development, plasticity, disease and injury. Nat Rev Neurosci. Mar. 2007;8(3):221-32.
Meltzer-Brody, et al., New insights into perinatal depression: pathogenesis and treatment during pregnancy andpostpartum. Dialogues Clin Neurosci. 2011;13(1):89-100.
Doornbos, et al. Sequential serotonin and noradrenalin associated processes involved in postpartum blues. Prog Neuropsychopharmacol Biol Psychiatry. Jul. 1, 2008;32(5):1320-5.
O'Hara, et al., Postpartum depression: what we know. J Clin Psychol 2009; 65(12): 1258-1269.

(Continued)

*Primary Examiner* — Jehanne S Sitton
(74) *Attorney, Agent, or Firm* — DLA Piper LLP (US)

(57) ABSTRACT

The present invention relates to the field of post-partum depression. More specifically, the present invention relates to the use of biomarkers to diagnose post-partum depression or predict a risk thereof. In a specific embodiment, a method for identifying a likelihood of PPD in a patient comprises the steps of (a) providing a sample from the patient; (b) measuring white blood cell type counts and DNA methylation levels of a panel of biomarkers in the sample collected from the patient, wherein the panel of biomarkers comprises HP1BP3 and TTC9B and the white blood cell type counts comprise monocytes and non-monocytes; and (c) identifying the patient as likely to develop PPD based on the relative DNA methylation levels at the biomarker loci relative to the ratio of monocytes:non-monocytes.

31 Claims, 10 Drawing Sheets

Specification includes a Sequence Listing.

(56) References Cited

OTHER PUBLICATIONS

Soufia, et al., SSRIs and pregnancy: a review of the literature. Encephale 2010; 36(6): 513-516.
Field, Prenatal depression effects on early development: a review. Infant Behav Dev 2011; 34(1): 1-14.
Breese Mccoy, Postpartum depress ion: an essential overview for the practitioner. South Med J 2011; 104(2): 128-132.
Cuijpers, et al., Psychological treatment of postpartum depression: a meta-analysis . J Clin Psychol 2008; 64( 1 ): 103- 118.
Hirst, et al., Postpartum major depression. Am Fam Physician 2010; 82(8): 926-933.
Marcus, Depression during pregnancy: rates, risks and consequences-Motherisk Update 2008. Can J Clin Pharmacol 2009; 16(1): e15-22.
Pinette, et al., The management of depression during pregnancy: a report from the American Psychiatric Association and the American College of Obstetricians and Gynecologists. Obstet Gynecol 2010; 115( 1): 188-189; author reply 189.
Studd, A guide to the treatment of depression in women by estrogens. Climacteric. Dec. 2011;14(6):637-42.
Bloch, et al., Effects of gonadal steroids in women with a history of postpa1tum depression. Am J Psychiatry 2000; 157(6): 924-930.
Bloch, et al., Cortisol response to ovine corticotropin-releasing hormone in a model of pregnancy and parturition in euthymic women with and without a history of postpartum depression. J Clin Endocrinol Metab 2005; 90(2): 695-699.
Kangaspeska, et al., Transient cyclical methylation of promoter DNA. Nature 2008; 452(7183): 112-115.
Kaminsky, et al., DNA methylation profiles in monozygotic and dizygotic twins. Nat Genet 2009; 41 (2): 240-245.
Schumacher, et al., Microarray-based DNA methylation profiling: technology and applications. Nucleic Acids Res 2006; 34(2): 528-542.
Houseman, et al., DNA methylation arrays as surrogate measures of cell mixture distribution. BMC Bioinformatics 2012; 13( I): 86.
Langfelder, et al., WGCNA: an R package for weighted correlation network analysis. BMC Bioinformatics 2008; 9: 559.
Walf, et al., Estradiol or diarylpropionitiile decrease anxiety-like behavior of wildtype, but not estrogen receptor beta knockout, mice. Behav Neurosci 2008; 122(5): 974-981.
Osterlund, et al., Estrogen action in mood and neurodegenerative disorders: estrogenic compounds with selective properties-the next generation of therapeutics. Endocrine 2005; 28(3): 235-242.
Lund, et al., Novel actions of estrogen receptorbeta on anxiety-related behaviors. Endocrinology 2005; 146(2): 797-807.
Walf, et al., Antidepressant effects of ERbeta-selective estrogen receptor modulators in the forced swim test. Pharmacol Biochem Behav 2004; 78(3): 523-529.
Walf, et al., ERbeta-selective estrogen receptor modulators produce antianxiety behavior when administered systemically to ovariectomized rats. Neuropsychopharmacology 2005; 30(9): 1598-1609.
Maclunsky, et al., The 17alpha and 17beta isomers of estradiol both induce rapid spine synapse formation in the CA 1 hippocampal subfield of ovariectomized female rats. Endocrinology 2005; 146(1): 287-293.
Ter Horst, Estrogen in the limbic system. Vitam Horm 2010; 82: 319-338.
Suda, et al., A postpartum model in rat: behavioral and gene expression changes induced by ovarian steroid deprivation. Biol Psychiatry 2008; 64(4): 311-319.
Green, et al., Adult hippocampal cell proliferation is suppressed with estrogen withdrawal after a hormone-simulated pregnancy. Horm Behav 2008; 54(1): 203-211.
Beissbarth, et al., GOstat: find statistically overrepresented Gene Ontologies within a group of genes. Bioinformatics 2004; 20(9): 1464-1465.
Reimand, et al., g:Profiler—a web-based toolset for functional profiling of gene lists from large-scale experiments. Nucleic Acids Res 2007; 35(Web Server issue): W 193-200.
Shimamiya, et al., Mood change and immune status of human subjects in a 10-day confinement study. Aviat Space Environ Med 2005; 76(5): 481-485.
Lutgendorf, et al., Depressed and anxious mood and T-cell cytokine expressing populations in ovarian cancer patients. Brain Behav Immun 2008; 22(6): 890-900.
Snel, et al., STRING: a web-server to retrieve and display the repeatedly occurring neighbourhood of a gene. Nucleic Acids Res 2000; 28(18): 3442-3444.
Guido, et al., Estrogen receptor beta (ERbeta) produces autophagy and necroptosis in human serninoma cell line through the binding of tl1e Spl on the phosphatase and tens in homo log deleted from chromosome 10 (PTEN) promoter gene. Cell Cycle 2012; 11(15): 2911-2921.
Bartella, et al., Estrogen receptor beta binds Spl and recruits a corepressor complex to the estrogen receptor alpha gene promoter. Breast Cancer Res Treat 2012; 134(2): 569-581.
Ruegg, et al., Epigenetic regulation of glucose transporter 4 by estrogen receptor beta. Mol Endocrinol 2011; 25(12): 2017-2028.
Vivar, et al., Estrogen receptor beta binds to and regulates three distinct classes of target genes. J Biol Chem 20 IO; 285(29): 22059-22066.
Ramanan, et al., Genome-wide pathway analysis of memo1y impairment in the Alzheimer's Disease Neuroimaging Initiative (ADNI) cohort implicates gene candidates, canonical pathways, and networks. Brain Imaging Behav 2012.
Nassa, et al., A large set of estrogen receptor beta-interacting proteins identified by tandem affinity purification in hormone-responsive human breast cancer cell nuclei. Proteomics 2011; 11 ( 1 ):159-165.
Cao, et al., Identification of tetratricopeptide repeat domain 9, a hormonally regulated protein. Biochem Biophys Res Commun 2006; 345(1 ): 3 I 0-3 I 7.
Gerges, et al., Independent functions of hsp90 in neurotransmitter release and in the continuous synaptic cycling of AMPA receptors. J Neurosci 2004; 24(20): 4758-4766.
Kuijpens, et al., Thyroid peroxidase antibodies during gestation are a marker for subsequent depression postpartum. Eur J Endocrinol 2001; 145(5): 579-584.
Skrundz, et al., Plasma oxytocin concentration dming pregnancy is associated with development of postpartum depression. Neuropsychopharmacology 2011; 36(9): 1886-1893.
Yim, et al., Prenatal beta-endorphin as an early predictor of postpartum depressive symptoms in euthymic women. J Affect Disord 2010; 125(1-3): 128-133.
Licinio, et al., Potential diagnostic markers for postpartum depression point out to altered immune signaling. Mol Psychiatry 2010; 15(1): 1.
Albacar, et al., Thyroid function 48h after delivery as a marker for subsequent postpartum depression. Psychoneuroendocrinology 2010; 35(5): 738-742.
Segman, et al., Blood mononuclear cell gene expression signature of postpartum depression. Mol Psychiatry 2010; 15(1): 93-100, 102.
Mcdonald, et al., Development of a prenatal psychosocial screening tool for post-partum depression and anxiety. Paediatr Perinat Epidemiol. Jul. 2012;26(4):316-27.
Austin, et al., The Antenatal Risk Questionnaire (ANRQ): Acceptability and use for psychosocial risk assessment in the maternity setting. Women Birth. Mar. 2013;26(1):17-25.
Tortajada, et al., Prediction of postpartum depression using multilayer perceptrons and pruning. Methods Inf Med. 2009;48(3):291-8.
Kim, et al., Prediction of postpartum depression by sociodemographic, obstetric and psychological factors: a prospective study. Psychiatry Clin Neurosci. Jun. 2008;62(3):331-40.
Kessler, et al., Sex and depression in the National Comorbidity Survey. I: Lifetime prevalence, chronicity and recurrence. J Affect Disord. Oct.-Nov. 1993;29(2-3):85-96.
Kessler, et al., Posttraumatic stress disorder in the National Comorbidity Survey. Arch Gen Psychiatry. Dec. 1995;52 (12):1048-60.
Weissman, et al., Depression in women: implications for health care research. Science. Aug. 11, 1995;269 (5225):799-801.

(56) References Cited

OTHER PUBLICATIONS

Bouma, et al., Stressful life events and depressive problems in early adolescent boys and girls: the influence of barental depression, temperament and family environment. J Affect Disord. Jan. 2008;105(1-3):185-93.
Kessler, et al., Epidemiology of women and depression. J Affect Disord. Mar. 2003,74(1):5-13.
Lee, et al., Clathrin adaptor AP2 and NSF interact with overlapping sites of GluR2 and play distinct roles in AMPA receptor trafficking and hippocampal LTD. Neuron. Nov. 14, 2002;36(4):661-74.
Scrandis, et al., Prepartum Depressive Symptoms Correlate Positively with CReactive Protein Levels and Negatively with Tryptophan Levels: A Preliminary Report. Int J Child Health Hum Dev. Aug. 2008;1(2):167-174.
Wong, et al., The role of epidermal growth factor and its receptors in mammalian CNS. Cytokine Growth Factor Rev. Apr.-Jun. 2004;15(2-3):147-56.
Kim, et al., Developmental regulation of Eed complex composition governs a switch in global histone modification in prain. J Biol Chem. Mar. 30, 2007;282(13):9962-72.
Abdelmohsen, et al., miR-375 inhibits differentiation of neurites by lowering HuD levels. Mol Cell Biol. Sep. 2010;30 (17):4197-210.
Favereaux, et al., Bidirectional integrative regulation of Cav1.2 calcium channel by microRNA miR-103: role in pain. EMBO J. Jul. 29, 2011;30(18):3830-41.
Nilsson, et al., Transcription factor AP-2 beta genotype and psychosocial adversity in relation to adolescent depressive symptomatology. J Neural Transm (Vienna). Mar. 2009;116(3):363-70.
Damberg, et al., Chronic pharmacological treatment with certain antidepressants alters the expression and DNA-binding activity of transcription factor AP-2. Life Sci. Dec. 29, 2000;68(6):669-78.
Bailara, et al., Decreased brain tryptophan availability as a partial determinant of post-partum blues. Psychoneuroendocrinology. Apr. 2006;31(3):407-13.
Gregoire, et al., Transdermal oestrogen for treatment of severe postnatal depression. Lancet. Apr. 6, 1996;347 (9006):930-3.
Moses-Kolko, et al., Transdermal estradiol for postpartum depression: a promising treatment option. Clin Obstet Gynecol. Sep. 2009; 52(3): 516-529.
Studd, et al., Reproductive depression. Gynecol Endocrinol. Mar. 2012;28 Suppl 1:42-5.
Douma, et al., Estrogen-related mood disorders: reproductive life cycle factors. ANS Adv Nurs Sci. Oct.-Dec. 2005;28 (4):364-75.
Tarantino, et al., Using animal models to disentangle the role of genetic, epigenetic, and environmental influences on behavioral outcomes associated with maternal anxiety and depression. Front Psychiatry. 2011; 2: 44.
Krishnan, et al., Animal models of depression: molecular perspectives. Curr Top Behav Neurosci. 2011;7:121-47.
Galea, et al., Estradiol alleviates depressive-like symptoms in a novel animal model of post-partum depression. Behav Brain Res. Jul. 2001;122(1):1-9.
Green, et al., Role of estradiol withdrawal in 'anhedonic' sucrose consumption: a model of postpartum depression. Physiol Behav. May 25, 2009;97(2):259-65.
Stoffel, et al., Ovarian hormone withdrawal-induced "depression" in female rats. Physiol Behav. Dec. 15, 2004;83 (3):505-13.
Beckley, et al., Progesterone receptor antagonist CDB-4124 increases depression-like behavior in mice without affecting locomotor ability. Psychoneuroendocrinology. Jul. 2011;36(6):824-33.
Beckley, et al., Inhibition of progesterone metabolism mimics the effect of progesterone withdrawal on forced swim lest immobility. Pharmacol Biochem Behav. Oct. 2007; 87(4): 412-419.
Andreen, et al., Sex steroid induced negative mood may be explained by the paradoxical effect mediated by GABAA modulators. Psychoneuroendocrinology. Sep. 2009;34(8):1121-32.
Backstrom, et al., Paradoxical effects of GABA-A modulators may explain sex steroid induced negative mood symptoms in some persons. Neuroscience. Sep. 15, 2011;191:46-54.
Walf, et al., Oestrogen receptor beta is involved in the actions of oestrogens in the brain for affective behaviour, but hot trophic effects in peripheral tissues. J Neuroendocrinol. Feb. 2010;22(2):141-51.
Pittenger, et al., Stress, depression, and neuroplasticity: a convergence of mechanisms. Neuropsychopharmacology. Jan. 2008;33(1):88-109.
Walf, et al., Administration of estrogen receptor beta-specific selective estrogen receptor modulators to the hippocampus decrease anxiety and depressive behavior of ovariectomized rats. Pharmacol Biochem Behav. Feb. 2007;86(2):407-14.
Ubin, et al., Epigenetic Mechanisms: Critical Contributors to Long-Term Memory Formation. Neuroscientist. Dec. 2011;17(6):616-32.
Marsden, et al., Stressor-induced NMDAR dysfunction as a unifying hypothesis for the aetiology, pathogenesis and comorbidity of clinical depression. Med Hypotheses. Oct. 2011;77(4):508-28.
Miller, et al., Covalent modification of DNA regulates memory formation. Neuron. Mar. 15, 2007;53(6):857-69.
Feng, et al., Dnmt1 and Dnmt3a maintain DNA methylation and regulate synaptic function in adult forebrain neurons. Nat Neurosci. Apr. 2010;13(4):423-30.
Levenson, et al., Evidence that DNA (cytosine-5) methyltransferase regulates synaptic plasticity in the hippocampus. J Biol Chem. Jun. 9, 2006;281(23):15763-73.
Nelson, et al., Activity-dependent suppression of miniature neurotransmission through the regulation of DNA methylation. J Neurosci. Jan. 9, 2008;28(2):395-406.
Chen, et al., Derepression of BDNF transcription involves calcium-dependent phosphorylation of MeCP2. Science. Oct. 31, 2003;302(5646):885-9.
Clark, et al., Sp1 binding is inhibited by (m)Cp(m)CpG methylation. Gene. Aug. 11, 1997;195(1):67-71.
Tsetsenis, et al., Rab3B protein is required for long-term depression of hippocampal inhibitory synapses and for hormal reversal learning. Proc Natl Acad Sci U S A. Aug. 23, 2011;108(34):14300-5.
Huang, et al., Genetic evidence for a protein-kinase-A-mediated presynaptic component in NMDA-receptor-dependent forms of long-term synaptic potentiation. Proc Natl Acad Sci U S A. Jun. 28, 2005;102(26):9365-70.
Fukushima, et al., Transforming growth factor-beta2 modulates synaptic efficacy and plasticity and induces phosphorylation of CREB in hippocampal neurons. Hippocampus. 2007;17(1):5-9.
Yano, et al., BDNF-mediated neurotransmission relies upon a myosin VI motor complex. Nat Neurosci. Aug. 2006;9 (8):1009-18.
Jahng, et al., Increased mesohippocampal dopaminergic activity and improved depression-like behaviors in maternally separated rats following repeated fasting/refeeding cycles. J Obes. 2012;2012:497101.
Hartz, et al., Genetic association of bipolar disorder with the beta(3) nicotinic receptor subunit gene. Psychiatr Genet. Apr. 2011;21(2):77-84.
Reuter, et al., Interaction of the cholinergic system and the hypothalamic-pituitary-adrenal axis as a risk factor for depression: evidence from a genetic association study. Neuroreport. Aug. 22, 2012;23(12):717-20.
Mason, et al., Location analysis for the estrogen receptor-alpha reveals binding to diverse ERE sequences and widespread binding within repetitive DNA elements. Nucleic Acids Res. Apr. 2010; 38(7): 2355-2368.
Vassallo, et al., Isoform-specific interaction of HP1 with human TAFII130. Proc Natl Acad Sci U S A. Apr. 30, 2002;99(9):5919-24.
Smallwood, et al., HP1-mediated silencing targets Pol II coactivator complexes. Nat Struct Mol Biol. Mar. 2008;15 (3):318-20.
Maison, et al., HP1 and the dynamics of heterochromatin maintenance. Nat Rev Mol Cell Biol. Apr. 2004;5 (4):296-304.
Ichimura, et al., Transcriptional repression and heterochromatin formation by MBD1 and MCAF/AM family proteins. J Biol Chem. Apr. 8, 2005;280(14):13928-35.
Kramar, et al., Estrogen promotes learning-related plasticity by modifying the synaptic cytoskeleton. Neuroscience. Jun. 3, 2013;239:3-16.

(56) References Cited

OTHER PUBLICATIONS

Kim, et al., Enhancement of rat hippocampal long-term potentiation by 17 beta-estradiol involves mitogen-activated protein kinase-dependent and -independent components. Neurosci Lett. Oct. 25, 2002;332(1):65-9.
Meltzer-Brody, et al., "Elevated carticotropin releasing hormone (CRH) during pregnancy and risk of postpartum depression (PPD)" The Journal of Clinical Endocrinology and Metabolism, (Jan. 2011), vol. 96, No. 1, pp. E40-E47.
Fuchikami, et al., "DNA methylation profiles of the brain-derived neurotrophic factor (BDNF) gene as a potent diagnostic biomarker in major depression", PLoSone (Aug. 2011) vol. 6, Issue 8, Article No. e23881, pp. 107.
Guintivano, et al., "Antenatal prediction of postpartum depression with blood DNA methylation biomarkers", Molecular Psychiatry, May 21, 2013, Advanced online publication, pp. 1-8.
Meltzer-Brody, "New insights into perinatal depression: pathogenesis and treatment during pregnancy an postpartum", Dialogues Clin Neurosci., 2011, vol. 13, No. 1, pp. 89-100.
Doornbos et al., "Sequential serotonin and noradrenalin associated processes involved in postpartum blues", Prog Neuropsychopharmacol Biol Psychiatry, Jul. 1, 2008, vol. 32, No. 5, pp. 1320-1325.
Bailara et al., "Decreased brain tryptophan availability as a partial determinant of post-partum blues", Psychoneuroendocrinology, Apr. 2006, vol. 31, No. 3, pp. 407-413.
Segman et al., "Blood mononuclear cell gene expression signature of postpartum depression", Mol Psychiatry, Jan. 2010, vol. 15, No. 1, pp. 93-100.
Houseman, E., "Dna methylation arrays as surrogate measures of cell mixture distribution" Bioinformatics 2012, 13:86.
Cottrell, S. "Molecular diagnostic applications of DNA methylation technology" Clinical Biochemistry 37 (2004) 595-604.
Jones, P., et al., "The Fundamental Role of Epigenetic Events in Cancer" Nature Reviews | Genetics vol. 3 | Jun. 2002.
Verma, M., "Genetic and epigenetic biomarkers in cancer diagnosis and identifying high risk populations" Critical Reviews in Oncology/Hematology 60 (2006) 9-18.

* cited by examiner

DNA METHYLATION BIOMARKERS OF POST-PARTUM DEPRESSION RISK

CROSS-REFERENCE TO RELATED APPLICATIONS

This application is a Continuation of U.S. patent application Ser. No. 14/439,468, filed Apr. 29, 2015, which is a 35 U.S.C. § 371 U.S. national entry of International Application PCT/US2013/068241, having an international filing date of Nov. 4, 2013, which claims the benefit of U.S. Provisional Application No. 61/721,660, filed Nov. 2, 2012, and U.S. Provisional Application 61/773,257, filed Mar. 6, 2013, the content of each of the aforementioned applications is herein incorporated by reference in their entirety.

STATEMENT OF GOVERNMENTAL INTEREST

This invention was made with government support under grant nos. MH074799 and MH093967 awarded by the National Institutes of Health. The government has certain rights in the invention.

FIELD OF THE INVENTION

The present invention relates to the field of post-partum depression. More specifically, the present invention relates to the use of biomarkers to diagnose post-partum depression or predict a risk thereof.

INCORPORATION-BY-REFERENCE OF MATERIAL SUBMITTED ELECTRONICALLY

This application contains a sequence listing. It has been submitted electronically via EFS-Web as an ASCII text file entitled "P12094-03_Sequence_Listing_ST25.txt." The sequence listing is 4,293 bytes in size, and was created on Oct. 31, 2013. It is hereby incorporated by reference in its entirety.

BACKGROUND OF THE INVENTION

Post partum depression (PPD) occurs in approximately 10-18% of women and results in significant morbidity to both mother and child, with offspring risks including low self-esteem, low intellectual skills, child abuse, and infanticide[1-6]. Women with mood disorders are at an increased risk of PPD[7], however, the benefits of psychiatric treatment must be carefully weighed against the potential risks of in utero exposure of the offspring to treatment. Antidepressant treatment during pregnancy can result in increased miscarriage rates in early pregnancy and have been associated with low birth weight, pre-term birth, and birth defects with some classes of antidepressants[8]. Limited information is available on the long term neurocognitive effects of in utero antidepressant exposure[8].

PPD occurs up to four weeks following parturition according to DSM-IV criteria and follows a dramatic drop in the circulating levels of estradiol (E2) and progesterone (P4). While depression risk is not predicted by serum levels of gonadal hormones in humans[9], rapid withdrawal from these hormones appears to be a key factor in establishing PPD. In a key experiment, women with a previous history of PPD subjected to supra-physiological doses of E2 and P4 experienced significantly depressed mood symptoms relative to controls upon hormone withdrawal[10, 11], suggesting that the at-risk population exhibits a predisposition to PPD through unknown mechanisms that is triggered by gonadal hormone withdrawal. DNA methylation may represent the link between estrogen and its effects on mood. Indeed, it has previously been demonstrated that E2 administration in vitro can modify DNA methylation at multiple locations downstream of an estrogen response element[12].

Given that fluctuations in estrogen coincide with PPD symptoms and can be antidepressant when administered as a treatment[7, 21-24], we hypothesized that predisposition to PPD risk is due to an altered sensitivity to estrogen mediated epigenetic changes that act in a cell autonomous fashion detectable in blood. In this study, we perform a multi-tiered translational approach to predicting PPD status in a prospective cohort using DNA methylation from both human blood and hippocampus of mice administered E2. We first define genomic regions of E2 mediated epigenetic change in E2 treated mice and investigated the relationship between E2-induced DNA methylation and PPD risk at syntenic regions in humans. Finally, we use E2-induced methylation models generated in the mice to predict PPD status in the humans.

SUMMARY OF THE INVENTION

The present invention is based, at least in part, on the discovery of a set of biomarkers capable of predicting post partum depression (PPD). To the inventors' knowledge, the present invention represents the first DNA methylation based biomarker set capable of predicting PPD. The genomic locations identified are not reported elsewhere as being associated with PPD. Other PPD biomarkers use DNA sequence variation, serum hormone levels, or questionnaires to attempt to predict PPD risk.

PPD occurs in approximately 10-18% of women and represents a serious health risk to both mothers and their offspring. The present inventors hypothesized that estrogen-mediated DNA methylation changes may contribute to PPD risk. Using mouse hippocampus, genomic regions where DNA methylation is reprogrammed by estrogen were identified. Investigation of these regions in second and third trimester blood of women with mood disorders identified a set of genes where DNA methylation levels predict PPD.

More specifically, the present invention provides a set of biomarkers capable of predicting PPD risk based on DNA methylation levels taken at a set of loci in from blood. The identification of these biomarkers was facilitated by a cross tissue and species analysis combining mouse hippocampal tissue and a prospective human sample consisting of second and third trimester blood of women who would go on to develop or not develop PPD. The present inventors hypothesized that differences in estrogen mediated epigenetic reprogramming may confer risk to PPD and that, due to the systemic nature of gonadal hormone levels, such changes would be detectable across tissues. Using the mouse hippocampus, genomic regions where DNA methylation is reprogrammed by estrogen were identified. Genomic locations exhibiting hippocampal E2 based DNA methylation programming were cross referenced with syntenic loci located on the human microarray. For each DMR, a logistic regression model was generated to predict PPD status in half of the human sample. An algorithm was then generated to combine biomarkers using linear discriminate analysis and the ability of the statistical model to predict PPD was tested on the remaining half of the human sample. Using a statistical model generated from this data, PPD status was predicted and an area under the receiver operator characteristic (ROC) curve of 0.91 was obtained. This algorithm was permuted to test for chance outcomes and a genome corrected p value of 0.041 was obtained. In certain embodiments, the identified biomarkers comprise the CpG dinucleotides located within the region chr1: 20986708-20986650 (strand –, human genome build hg18), chr 19: 45416573 (strand +, human genome build hg18), chr3:8785134-8785171 (strand –, human genome build hg18), and/or region chr20: 42971786-42971857 (strand +, human genome build hg18).

The genes proximal to the identified biomarkers can be linked with antidepressant functions in the hippocampus. Cumulatively, a set of markers capable of predicting PPD risk to a high degree of accuracy has been generated. In certain embodiments, the present invention provides a blood test for women in either their 1$^{st}$, 2nd or 3rd trimester of pregnancy that predicts their risk of developing post partum depression after parturition.

Accordingly, in one aspect, the present invention provides methods for predicting post partum depression (PPD) in a patient. In one embodiment, the method comprises (a) providing a sample from the patient; (b) measuring white blood cell type counts and the DNA methylation levels of one or more biomarkers in the sample collected from the patient; and (c) predicting PPD in the patient based on the relative DNA methylation levels at the one or more biomarker loci relative to the proportion of differing white blood cell types. In a specific embodiment, the one or more biomarkers comprises heterochromatin protein 1, binding protein 3 (HP1BP3), tetratricopeptide repeat domain 9B (TTC9B), oxytocin receptor (OXTR) and poly(A) binding protein, cytoplasmic 1-like (PABPC1L). In a more specific embodiment, the one or more biomarkers comprises HP1BP3. In a further embodiment, the HP1BP3 biomarker loci comprises CpG dinucleotides located within the region chr1: 20986708-20986650 on the minus strand (human genome build hg18).

In another embodiment, the one or more biomarkers comprises TTC9B. More specifically, the TTC9B biomarker loci can comprise CpG dinucleotides located at chr19: 45416573 on the plus strand (human genome build hg18). In yet another embodiment, the one or more biomarkers comprises OXTR. In certain embodiments, the OXTR biomarker loci comprises CpG dinucleotides located within the region chr3:8785134-8785171 on the minus strand (human genome build hg18).

In particular embodiments, the sample is a blood or serum sample. In certain embodiments, the proportion of differing white blood cell types comprises the ratio of monocytes: non-monocytes. In other embodiments, the predicting step is performed using a linear model.

The present invention also provides methods for determining the risk of developing PPD in a patient comprising the steps of (a) providing a sample from the patient; (b) measuring white blood cell type counts and the DNA methylation levels of a panel of biomarkers in the sample collected from the patient, wherein the panel of biomarkers comprises HP1BP3 and TTC9B; and (c) determining that the patient is at risk for developing PPD based on the relative DNA methylation levels at the biomarker loci relative to the proportion of differing white blood cell types. In one embodiment, the panel of biomarkers further comprises PABPC1L. In a more specific embodiment, the PABPC1L biomarker comprises CpG dinucleotides located within the region chr20: 42971786-42971857 on the positive strand (human genome build hg18).

In another embodiment, the HP1BP3 biomarker loci comprises CpG dinucleotides located within the region chr1: 20986708-20986650 on the minus strand (human genome build hg18). In yet another embodiment, the TTC9B biomarker loci comprises CpG dinucleotides located at chr19: 45416573 on the plus strand (human genome build hg18). In a further embodiment, the panel of biomarkers further comprises OXTR. More specifically, the OXTR biomarker loci can comprise CpG dinucleotides located within the region chr3:8785134-8785171 on the minus strand (human genome build hg18).

In particular embodiments, the sample is a blood or serum sample. In certain embodiments, the proportion of differing white blood cell types comprises the ratio of monocytes: non-monocytes. In particular embodiments, the determining step is performed using a linear model.

In certain embodiments, the present invention provides a method for identifying a likelihood of PPD in a patient comprising the steps of (a) providing a sample from the patient; (b) measuring white blood cell type counts and DNA methylation levels of a panel of biomarkers in the sample collected from the patient, wherein the panel of biomarkers comprises HP1BP3 and TTC9B and the white blood cell type counts comprise monocytes and non-monocytes; and (c) identifying the patient as likely to develop PPD based on the relative DNA methylation levels at the biomarker loci relative to the ratio of monocytes:non-monocytes. In a specific embodiment, the panel of biomarkers further comprises PABPC1L. In a more specific embodiment, the PABPC1L biomarker comprises CpG dinucleotides located within the region chr20: 42971786-42971857 on the positive strand (human genome build hg18). In another specific embodiment, the HP1BP3 biomarker loci comprises CpG dinucleotides located within the region chr1: 20986708-20986650 on the minus strand (human genome build hg18). In yet another embodiment, the TTC9B biomarker loci comprises CpG dinucleotides located at chr19: 45416573 on the plus strand (human genome build hg18). The sample can be a blood or serum sample.

In the methods described herein, the identifying step can be performed using a linear model with DNA methylation at HP1BP3 interacting with the ratio of monocytes:non-monocytes and DNA methylation at TTC9B is included as an additive covariate. In another embodiment, the identifying step is performed using a linear model with DNA methylation at HP1BP3 and TTC9B included as additive covariates and the ratio of monocytes:non-monocytes added as an interacting component. In yet another embodiment, the identifying step is performed using a linear model and DNA methylation at OXTR is used in place of the ratio of monocytes:non-monocytes. In a more specific embodiment, the OXTR biomarker loci comprises CpG dinucleotides located at chr3:8785134-8785171 on the minus strand (human genome build hg18).

In an alternative embodiment, the identifying step is performed using a linear model and DNA methylation at PABPC1L is used in place of the ratio of monocytes:non-monocytes. For example, in certain embodiments, the PABPC1L biomarker comprises CpG dinucleotides located within the region chr20: 42971786-42971857 on the positive strand (human genome build hg18).

The present invention also contemplates that the addition of the total test score from the Pittsburgh Sleep Quality Index (PSQI) scale taken at the time of sample draw from the patient is used as an additive or interactive covariate in the model to improve prediction accuracy. In another embodiment, the addition of the total test score from the Clinical Global Impression Scale (CGIS) scale taken at the time of sample draw from the patient is used as an additive or interactive covariate in the model to improve prediction accuracy. In a further embodiment, the addition of the total test score from the Perceived Stress Scale (PSS) scale taken at the time of sample draw from the patient is used as an additive or interactive covariate in the model to improve prediction accuracy. In an alternative embodiment, the addition of DNA methylation biomarker proxies of psychological scale metrics from Table 6 are used in place of test scale metrics.

In a further aspect, the present invention provides methods for predicting post partum depression (PPD) in a patient. In one embodiment, the method comprises the steps of (a) providing a blood sample from the patient; (b) measuring the DNA methylation levels of a panel of biomarkers and white blood cell type counts in the sample collected from the patient, wherein the panel of biomarkers comprises HP1BP3 and TTC9B; and (c) comparing the methylation levels of the one or more biomarkers with predefined methylation levels of the same biomarkers that correlate to a patient having PPD and predefined methylation levels of the same biomarkers that correlate to a patient not having PPD, wherein a correlation to one of the predefined methylation levels provides the prediction. In another embodiment, the panel of biomarkers further comprises PABPC1L or OXTR.

The present invention further provides methods for determining the PPD status in a patient. In a specific embodiment, the method comprises the steps of (a) providing a sample from the patient; (b) measuring the DNA methylation levels of a panel of biomarkers and white blood cell type counts in the sample collected from the patient, wherein the panel of biomarkers comprises PABPC1L, HP1BP3, TTC9B and/or OXTR; and (c) comparing the methylation levels of the panel of biomarkers with predefined methylation levels of the same panel of biomarkers that correlate to one or more PPD statuses selected from the group consisting of having PPD, not having PPD, progressing PPD, and regressing PPD, wherein a correlation to one of the predefined methylation levels determines the PPD status of the patient.

The present invention also provides a method for diagnosing PPD in a patient comprising the steps of (a) providing a sample from the patient; (b) measuring white blood cell type counts and the DNA methylation levels of a panel of biomarkers in the sample collected from the patient, wherein the panel of biomarkers comprises HP1BP3 and TTC9B and the white blood cell type counts comprise monocytes and non-monocytes; and (c) diagnosing the patient as having PPD based on the relative DNA methylation levels at the biomarker loci relative to the proportion of monocytes:non-monocytes.

The present invention also contemplates that an area under the receiver operator characteristic curve analysis can be used to predict, determine the risk of developing, identify a likelihood of, or diagnose, PPD in the patient. In other embodiments, a linear discriminant analysis is used to predict, determine the risk of developing, identify a likelihood of, or diagnose, PPD.

In another aspect, the present invention provides diagnostic kits. In one embodiment, a diagnostic kit for determining PPD status in a patient comprises (a) a substrate for collecting a biological sample from the patient; and (b) means for measuring the DNA methylation levels of one or more biomarkers selected from the group consisting of HP1BP3, TTC9B, OXTR and/or PABPC1L. In a specific embodiment, the means for measuring the methylation levels of one or more biomarkers are oligonucleotide primers specific for amplifying methylated regions of the biomarkers. In a more specific embodiment, the primers comprise one or more of SEQ ID NOS:1-22.

BRIEF DESCRIPTION OF THE FIGURES

(FIG. 1A) Volcano plot depicting the difference in DNA methylation between women who suffered PPD vs. those who did not (x-axis) against the negative natural log of the p value of association between groups (y-axis). (FIG. 1B) A volcano plot depicting DNA methylation differences between the ovariectomy (OVX) and OVX+E2 groups per DMR (X-axis) and the natural log of the p value for each comparison. Horizontal red lines depicts the significance threshold of 5%. (FIG. 1C) Scatter plot of the −log of the p value of association to discovery sample PPD status and the effect size of E2 mediated DNA methylation change at 103 overlapping loci nominally significant in both humans and mice. (FIG. 1D) Scatter plot of the difference between PPD and non-PPD women in the discovery sample (y-axis) as a function of that in the replication sample (x-axis).

(FIG. 3A) Boxplot of the ratio of granulocyte percentage over the sum of T cell, B cell, and monocyte percentages as a function of prepartum depression status and PPD diagnosis. (FIG. 3B) Boxplot of the HP1BP3 DNA methylation percentage as a function of prepartum depression status and PPD diagnosis. (FIG. 3C) Scatterplot of the ratio of monocyte percentage over the sum of WBC and monocyte percentages as a function of the HP1BP3 DNA methylation percentage. (FIG. 3D) ROC curve of the sensitivity (y-axis) vs. specificity (x-axis) of PPD prediction from the linear model of the HP1BP3 DNA methylation and cell-type ratio interaction, with TTC9B DNA methylation as a covariate. The solid line represents the ROC curve from the proxy based cell proportion measurement and the dashed line represents that of the CBC derived subsample.

(FIG. 5A) MEME and TOMTOM motif plot depicting motif enrichment analysis using Multiple EM for Motif Elucidation software (MEME) of 400 bp sequences surrounding the top 100 significant E2 DMRs. A significant enrichment for the SP-1 transcription factor binding motif was identified (JASPAR_CORE_2009, MA0079.2, E value=0.038, p=4.4×

$10^{-5}$, q=0.015). (FIG. 5B) To validate that the identified DMRs were indicative of true biological changes, we selected mean DNA methylation of an identified DMR in the promoter of the hippocampally expressed ERβ gene as our target for array wide correlation. As ERβ expression has been shown to be dependent on promoter DNA methylation status[38], we expected epigenetic regions correlated with the ERβ promoter to demonstrate an over-representation of the ER binding motif. Motif enrichment analysis of 400 bp surrounding the top 100 ERβ correlating sequences identified a significant enrichment for the SP1 binding motif (JASPAR_CORE_2009, MA0112.2, E-value=0.0015, p=$1.7\times10^{-6}$, q=0.0015) as well as for a nominally significant enrichment of the estrogen receptor binding motif (JASPAR_CORE_2009, MA0112.2, E-value=0.15, p=$1.7\times10^{-4}$, q=0.30).

(FIG. 6A) Schematic representation of the algorithm used to identify a linear discriminant model of HP1BP3 and TTC9B DNA methylation predictive of PPD status. Red letters represent overlapping CG dinucleotide. (FIG. 6 B) Receiver operator characteristic (ROC) curves depicting the true positive rate (y-axis) as a function of the false positive rate (x-axis) for the prediction of PPD status using the linear discriminant model generated in panel A. Area under the ROC curves are depicted and represent the prediction accuracy expected at predicting PPD status from two dichotomously affected individuals based on DNA methylation from $2^{nd}$ or $3^{rd}$ trimester blood DNA methylation at HP1BP3 and TTC9B.

(FIG. 8A) Cluster dendrogram of co-regulated networks identified in 13,091 nominally significant loci by WGCNA. (FIG. 8B) Heatmap of correlation statistics of identified modules with HP1BP3 and TTC9B DNA methylation. (FIG. 8C) Scatter plot of a metric of locus specific significance for association to the PPD phenotype (y-axis) as a function of the degree of module membership (x-axis) for the first module commonly identified for both HP1BP3 and TTC9B (Spearman's Rho=0.22, p=$1.7\times10^{-105}$). (FIG. 8D) Scatter plot of a metric of locus specific significance for association to the PPD phenotype (y-axis) as a function of the degree of module membership (x-axis) for the first module commonly identified for both HP1BP3 and TTC9B (Spearman's Rho=0.18, p=$3.6\times10^{-9}$). Positive correlations denote that loci with higher module membership represent network 'hub' loci and are associated more strongly with phenotype.

(FIG. 9A) Heatmap of correlation statistics of identified modules by WGCNA with HP1BP3 and TTC9B DNA methylation in 3,606 top mouse E2 DMRs depicting a positive relationship between HP1BP3 and TTC9B co-regulated modules. A single module overlapping between the two loci was identified (Module 1: HP1BP3 Rho=−0.85, p=0.0017. TTC9B Rho=−0.63, p=0.047). No enriched KEGG pathways were identified; however GO analysis demonstrated an enrichment for GO:0030036 'actin cytoskeleton organization and biogenesis' (Observed frequency=0.12, expected frequency=0.033, p=0.024). In contrast to the human samples, module association statistics across associated networks between the two loci in the mouse dataset were positively correlated (Spearman's Rho=0.92, p=$2.2\times10^{-16}$) suggesting that under normal conditions, HP1BP3 and TTC9B are co-regulated in the hippocampus in response to E2. (FIG. 9B) Heatmap of correlation statistics of identified modules with HP1BP3 and TTC9B DNA methylation in 13,091 loci in non-PPD cases only. Results depict the positive relationship (Spearman's Rho=0.53, p=$3.8\times10^{-11}$) observed between HP1BP3 and TTC9B co-regulated modules. (FIG. 9C) Heatmap of correlation statistics of identified modules with HP1BP3 and TTC9B DNA methylation in 13,091 loci in non-PPD cases only. Results depict the negative relationship (Spearman's Rho=−0.2, p=0.0043) between HP1BP3 and TTC9B co-regulated modules. The direction of module correlation in the PPD cases is consistent with the proposed heightened sensitivity to E2 mediated epigenetic reprogramming in the PPD group.

DETAILED DESCRIPTION OF THE INVENTION

Figures 1A, 1B, 1C, 1D:
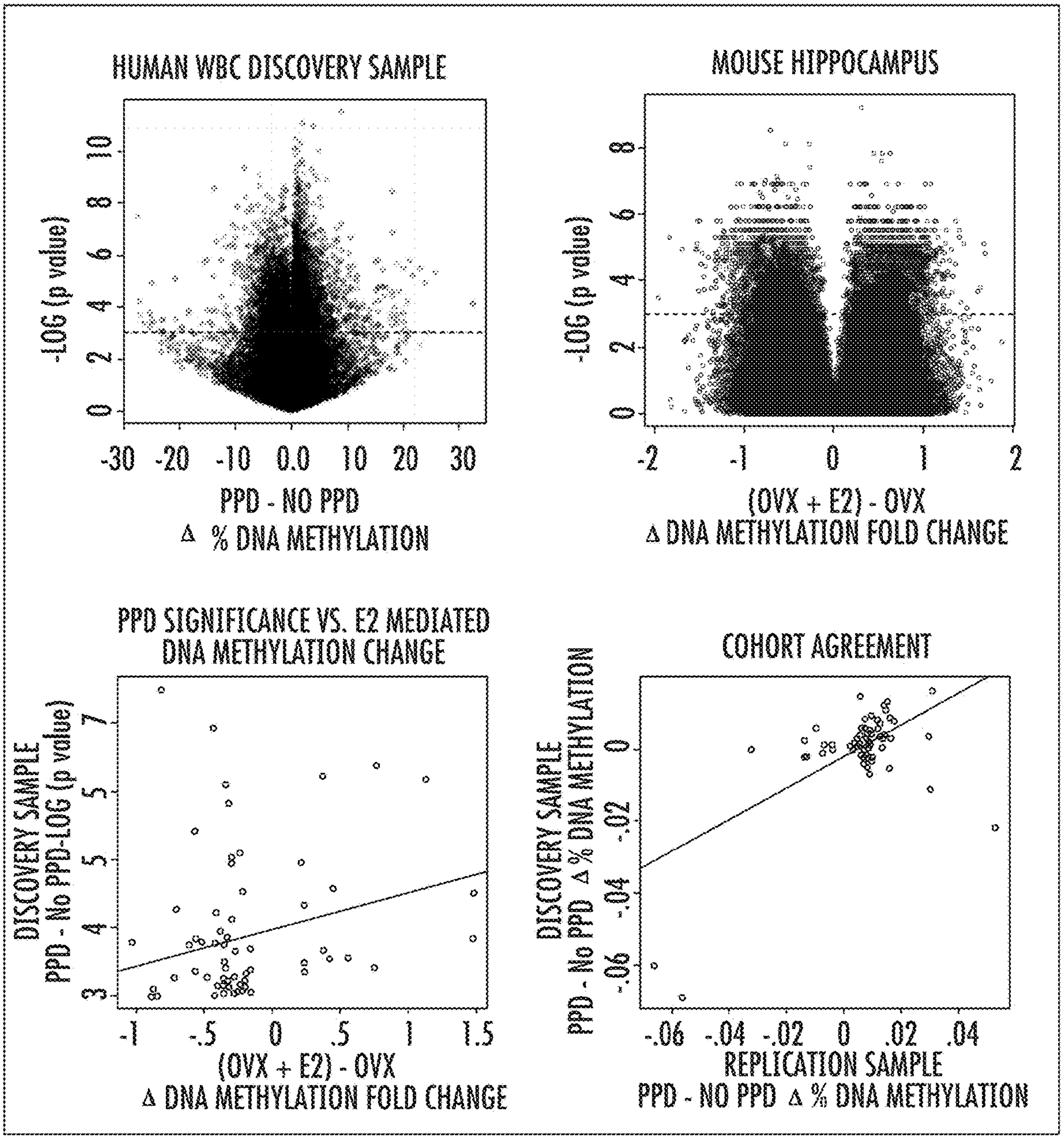
FIG. 1A-1D. E2 mediated DNA methylation change is associated with PPD risk.

It is understood that the present invention is not limited to the particular methods and components, etc., described herein, as these may vary. It is also to be understood that the terminology used herein is used for the purpose of describing particular embodiments only, and is not intended to limit the scope of the present invention. It must be noted that as used herein and in the appended claims, the singular forms "a," "an," and "the" include the plural reference unless the context clearly dictates otherwise. Thus, for example, a reference to a "protein" is a reference to one or more proteins, and includes equivalents thereof known to those skilled in the art and so forth.

Unless defined otherwise, all technical and scientific terms used herein have the same meaning as commonly understood by one of ordinary skill in the art to which this invention belongs. Specific methods, devices, and materials are described, although any methods and materials similar or equivalent to those described herein can be used in the practice or testing of the present invention.

All publications cited herein are hereby incorporated by reference including all journal articles, books, manuals, published patent applications, and issued patents. In addition, the meaning of certain terms and phrases employed in the specification, examples, and appended claims are provided. The definitions are not meant to be limiting in nature and serve to provide a clearer understanding of certain aspects of the present invention.

I. Definitions

As used herein, the term "comparing" refers to making an assessment of how the methylation status, proportion, level or cellular localization of one or more biomarkers in a sample from a patient relates to the methylation status, proportion, level or cellular localization of the corresponding one or more biomarkers in a standard or control sample. For example, "comparing" may refer to assessing whether the methylation status, proportion, level, or cellular localization of one or more biomarkers in a sample from a patient is the same as, more or less than, or different from the methylation status, proportion, level, or cellular localization of the corresponding one or more biomarkers in standard or control sample. More specifically, the term may refer to assessing whether the methylation status, proportion, level, or cellular localization of one or more biomarkers in a sample from a patient is the same as, more or less than, different from or otherwise corresponds (or not) to the methylation status, proportion, level, or cellular localization of predefined biomarker levels that correspond to, for example, a patient having PPD, at risk for developing PPD, not having PPD, is responding to treatment for PPD, is not responding to treatment for PPD, is/is not likely to respond to a particular PPD treatment, or having/not having another disease or condition. In a specific embodiment, the term "comparing" refers to assessing whether the methylation level of one or more biomarkers of the present invention in a sample from a patient is the same as, more or less than, different from other otherwise correspond (or not) to methylation levels of the same biomarkers in a control sample (e.g., predefined levels that correlate to uninfected individuals, standard PPD levels, etc.).

As used herein, the terms "indicates" or "correlates" (or "indicating" or "correlating," or "indication" or "correlation," depending on the context) in reference to a parameter, e.g., a modulated proportion, level, or cellular localization in a sample from a patient, may mean that the patient has PPD. In specific embodiments, the parameter may comprise the methylation status or level of one or more biomarkers of the present invention. A particular set or pattern of methylation of one or more biomarkers may indicate that a patient has PPD (i.e., correlates to a patient having PPD) or is at risk of developing PPD. In other embodiments, a particular set or pattern of methylation of one or more biomarkers may be correlated to a patient being unaffected. In certain embodiments, "indicating," or "correlating," as used according to the present invention, may be by any linear or non-linear method of quantifying the relationship between methylation levels of biomarkers to a standard, control or comparative value for the assessment of the diagnosis, prediction of PPD or PPD progression, assessment of efficacy of clinical treatment, identification of a patient that may respond to a particular treatment regime or pharmaceutical agent, monitoring of the progress of treatment, and in the context of a screening assay, for the identification of an anti-PPD therapeutic.

The terms "patient," "individual," or "subject" are used interchangeably herein, and refer to a mammal, particularly, a human. The patient may have mild, intermediate or severe disease. The patient may be an individual in need of treatment or in need of diagnosis based on particular symptoms or family history. In some cases, the terms may refer to treatment in experimental animals, in veterinary application, and in the development of animal models for disease, including, but not limited to, rodents including mice, rats, and hamsters; and primates.

The terms "measuring" and "determining" are used interchangeably throughout, and refer to methods which include obtaining a patient sample and/or detecting the methylation status or level of a biomarker(s) in a sample. In one embodiment, the terms refer to obtaining a patient sample and detecting the methylation status or level of one or more biomarkers in the sample. In another embodiment, the terms "measuring" and "determining" mean detecting the methylation status or level of one or more biomarkers in a patient sample. Measuring can be accomplished by methods known in the art and those further described herein including, but not limited to, quantitative polymerase chain reaction (PCR). The term "measuring" is also used interchangeably throughout with the term "detecting."

The term "methylation" refers to cytosine methylation at positions C5 or N4 of cytosine, the N6 position of adenine or other types of nucleic acid methylation. In vitro amplified DNA is unmethylated because in vitro DNA amplification methods do not retain the methylation pattern of the amplification template. However, "unmethylated DNA" or "methylated DNA" can also refer to amplified DNA whose original template was unmethylated or methylated, respectively. By "hypermethylation" or "elevated level of methylation" is meant an increase in methylation of a region of DNA (e.g., a biomarker of the present invention) that is considered statistically significant over levels of a control population. "Hypermethylation" or "elevated level of methylation" may refer to increased levels seen in a patient over time.

In particular embodiments, a biomarker would be unmethylated in a normal sample (e.g., normal or control tissue without disease, or normal or control body fluid, stool, blood, serum, amniotic fluid), most importantly in healthy stool, blood, serum, amniotic fluid or other body fluid. In other embodiments, a biomarker would be hypermethylated in a sample from a patient having or at risk of PPD, preferably at a methylation frequency of at least about 50%, at least about 60%, at least about 70%, at least about 75%, at least about 80%, at least about 85%, at least about 90%, at least about 95%, or about 100%.

A "methylation profile" refers to a set of data representing the methylation states or levels of one or more loci within a molecule of DNA from e.g., the genome of an individual or cells or sample from an individual. The profile can indicate the methylation state of every base in an individual, can comprise information regarding a subset of the base pairs (e.g., the methylation state of specific restriction enzyme recognition sequence) in a genome, or can comprise information regarding regional methylation density of each locus. In some embodiments, a methylation profile refers to the methylation states or levels of one or more biomarkers described herein, including HP1BP3 and TTC9B. In more specific embodiments, a methylation profile refers to the methylation states of levels of the promoter regions of HP1BP3 and TTC9B. In even more specific embodiments, a methylation profile refers to the methylation states of levels of CpG dinucleotides located within the region chr1:20986708-20986650 (human genome build hg18) and/or CpG dinucleotides located at chr19:45416573 (human genome build hg18).

The terms "methylation status" or "methylation level" refers to the presence, absence and/or quantity of methylation at a particular nucleotide, or nucleotides within a portion of DNA. The methylation status of a particular DNA sequence (e.g., a DNA biomarker or DNA region as described herein) can indicate the methylation state of every base in the sequence or can indicate the methylation state of a subset of the base pairs (e.g., of cytosines or the methylation state of one or more specific restriction enzyme recognition sequences) within the sequence, or can indicate information regarding regional methylation density within the sequence without providing precise information of where in the sequence the methylation occurs. The methylation status can optionally be represented or indicated by a "methylation value" or "methylation level." A methylation value or level can be generated, for example, by quantifying the amount of intact DNA present following restriction digestion with a methylation dependent restriction enzyme. In this example, if a particular sequence in the DNA is quantified using quantitative PCR, an amount of template DNA approximately equal to a mock treated control indicates the sequence is not highly methylated whereas an amount of template substantially less than occurs in the mock treated sample indicates the presence of methylated DNA at the sequence. Accordingly, a value, i.e., a methylation value, for example from the above described example, represents the methylation status and can thus be used as a quantitative indicator of methylation status. Ibis is of particular use when it is desirable to compare the methylation status of a sequence in a sample to a threshold value.

A "methylation-dependent restriction enzyme" refers to a restriction enzyme that cleaves or digests DNA at or in proximity to a methylated recognition sequence, but does not cleave DNA at or near the same sequence when the recognition sequence is not methylated. Methylation-dependent restriction enzymes include those that cut at a methylated recognition sequence (e.g., DpnI) and enzymes that cut at a sequence near but not at the recognition sequence (e.g., McrBC). For example, McrBC's recognition sequence is 5' RmC (N40-3000) RmC 3' where "R" is a purine and "mC" is a methylated cytosine and "N40-3000" indicates the distance between the two RmC half sites for which a restriction event has been observed. McrBC generally cuts close to one half-site or the other, but cleavage positions are typically distributed over several base pairs, approximately 30 base pairs from the methylated base. McrBC sometimes cuts 3' of both half sites, sometimes 5' of both half sites, and sometimes between the two sites. Exemplary methylation-dependent restriction enzymes include, e.g., McrBC, McrA, MrrA, BisI, GlaI and DpnI. One of skill in the art will appreciate that any methylation-dependent restriction enzyme, including homologs and orthologs of the restriction enzymes described herein, is also suitable for use in the present invention.

A "methylation-sensitive restriction enzyme" refers to a restriction enzyme that cleaves DNA at or in proximity to an unmethylated recognition sequence but does not cleave at or in proximity to the same sequence when the recognition sequence is methylated. Exemplary methylation-sensitive restriction enzymes are described in, e.g., McClelland et al., 22(17) Nucleic Acids Res. 3640-59 (1994) and http://rebase.neb.com. Suitable methylation-sensitive restriction enzymes that do not cleave DNA at or near their recognition sequence when a cytosine within the recognition sequence is methylated at position $C^5$ include, e.g., Aat II, Aci I, Acd I, Age I, Alu I, Asc I, Ase I, AsiS I, Bbe I, BsaA I, BsaH I, BsiE I, BsiW I, BsrF I, BssH II, BssK I, BstB I, BstN I, BstU I, Cla I, Eae I, Eag I, Fau I, Fse I, Hha I, HinP1 I, HinC II, Hpa II, Hpy99 I, HpyCH4 IV, Kas I, Mbo I, Mlu I, MapA1 I, Msp I, Nae I, Nar I, Not I, Pml I, Pst I, Pvu I, Rsr II, Sac II, Sap I, Sau3A I, Sfl I, Sfo I, SgrA I, Sma I, SnaB I, Tsc I, Xma I, and Zra I. Suitable methylation-sensitive restriction enzymes that do not cleave DNA at or near their recognition sequence when an adenosine within the recognition sequence is methylated at position $N^6$ include, e.g., Mbo I. One of skill in the art will appreciate that any methylation-sensitive restriction enzyme, including homologs and orthologs of the restriction enzymes described herein, is also suitable for use in the present invention. One of skill in the art will further appreciate that a methylation-sensitive restriction enzyme that fails to cut in the presence of methylation of a cytosine at or near its recognition sequence may be insensitive to the presence of methylation of an adenosine at or near its recognition sequence. Likewise, a methylation-sensitive restriction enzyme that fails to cut in the presence of methylation of an adenosine at or near its recognition sequence may be insensitive to the presence of methylation of a cytosine at or near its recognition sequence. For example, Sau3AI is sensitive (i.e., fails to cut) to the presence of a methylated cytosine at or near its recognition sequence, but is insensitive (i.e., cuts) to the presence of a methylated adenosine at or near its recognition sequence. One of skill in the art will also appreciate that some methylation-sensitive restriction enzymes are blocked by methylation of bases on one or both strands of DNA encompassing of their recognition sequence, while other methylation-sensitive restriction enzymes are blocked only by methylation on both strands, but can cut if a recognition site is hemi-methylated.

The terms "sample," "patient sample," "biological sample," and the like, encompass a variety of sample types obtained from a patient, individual, or subject and can be used in a diagnostic or monitoring assay. The patient sample may be obtained from a healthy subject, a diseased patient or a patient having associated symptoms of PPD. Moreover, a sample obtained from a patient can be divided and only a portion may be used for diagnosis. Further, the sample, or a portion thereof, can be stored under conditions to maintain sample for later analysis. The definition specifically encompasses blood and other liquid samples of biological origin (including, but not limited to, peripheral blood, serum, plasma, urine, saliva, amniotic fluid, stool and synovial fluid), solid tissue samples such as a biopsy specimen or tissue cultures or cells derived therefrom and the progeny thereof. In a specific embodiment, a sample comprises a blood sample. In another embodiment, a serum sample is used. In another embodiment, a sample comprises amniotic fluid. In yet another embodiment, a sample comprises amniotic fluid. The definition also includes samples that have been manipulated in any way after their procurement, such as by centrifugation, filtration, precipitation, dialysis, chromatography, treatment with reagents, washed, or enriched for certain cell populations. The terms further encompass a clinical sample, and also include cells in culture, cell supernatants, tissue samples, organs, and the like. Samples may also comprise fresh-frozen and/or formalin-fixed, paraffin-embedded tissue blocks, such as blocks prepared from clinical or pathological biopsies, prepared for pathological analysis or study by immunohistochemistry.

Various methodologies of the instant invention include a step that involves comparing a value, level, feature, characteristic, property, etc. to a "suitable control," referred to interchangeably herein as an "appropriate control" or a "control sample." A "suitable control," "appropriate control" or a "control sample" is any control or standard familiar to one of ordinary skill in the art useful for comparison purposes. In one embodiment, a "suitable control" or "appropriate control" is a value, level, feature, characteristic, property, etc., determined in a cell, organ, or patient, e.g., a control or normal cell, organ, or patient, exhibiting, for example, normal traits. For example, the biomarkers of the present invention may be assayed for their methylation level in a sample from an unaffected individual (UI) or a normal control individual (NC) (both terms are used interchangeably herein). In another embodiment, a "suitable control" or "appropriate control" is a value, level, feature, characteristic, property, etc. determined prior to performing a therapy (e.g., a PPD treatment) on a patient. In yet another embodiment, a transcription rate, mRNA level, translation rate, protein level, biological activity, cellular characteristic or property, genotype, phenotype, etc. can be determined prior to, during, or after administering a therapy into a cell, organ, or patient. In a further embodiment, a "suitable control" or "appropriate control" is a predefined value, level, feature, characteristic, property, etc. A "suitable control" can be a methylation profile of one or more biomarkers of the present invention that correlates to PPD, to which a patient sample can be compared. The patient sample can also be compared to a negative control, i.e., a methylation profile that correlates to not having PPD.

II. Hypermethylated Biomarkers and Detection Thereof

The biomarkers of the present invention are differentially methylated in PPD versus normal tissue. Such biomarkers can be used individually as diagnostic tool, or in combination as a biomarker panel. In particular embodiments, the biomarkers include HP1BP3 and TTC9B. In more specific embodiments, the biomarkers comprise the promoter regions of HP1BP3 and TTC9B. In even more specific embodiments, the biomarkers comprise CpG dinucleotides located within the region chr1: 20986708-20986650 (human genome build hg18) (HP1BP3) and/or CpG dinucleotides located at chr19:45416573 (human genome build hg18) (TTC9B). The sequences of these biomarkers are publicly available.

The DNA biomarkers of the present invention comprise fragments of a polynucleotide (e.g., regions of genome polynucleotide or DNA) which likely contain CpG island(s), or fragments which are more susceptible to methylation or demethylation than other regions of genome DNA. The term "CpG islands" is a region of genome DNA which shows higher frequency of 5'-CG-3' (CpG) dinucleotides than other regions of genome DNA. Methylation of DNA at CpG dinucleotides, in particular, the addition of a methyl group to position 5 of the cytosine ring at CpG dinucleotides, is one of the epigenetic modifications in mammalian cells. CpG islands often harbor the promoters of genes and play a pivotal role in the control of gene expression. In normal tissues CpG islands are usually unmethylated, but a subset of islands becomes methylated during the development of a disease or condition (e.g., PPD).

There are a number of methods that can be employed to measure, detect, determine, identify, and characterize the methylation status/level of a biomarker (i.e., a region/fragment of DNA or a region/fragment of genome DNA (e.g., CpG island-containing region/fragment)) in the development of a disease or condition (e.g., PPD) and thus diagnose the onset, presence or status of the disease or condition.

In some embodiments, methods for detecting methylation include randomly shearing or randomly fragmenting the genomic DNA, cutting the DNA with a methylation-dependent or methylation-sensitive restriction enzyme and subsequently selectively identifying and/or analyzing the cut or uncut DNA. Selective identification can include, for example, separating cut and uncut DNA (e.g., by size) and quantifying a sequence of interest that was cut or, alternatively, that was not cut. See. e.g., U.S. Pat. No. 7,186,512. Alternatively, the method can encompass amplifying intact DNA after restriction enzyme digestion, thereby only amplifying DNA that was not cleaved by the restriction enzyme in the area amplified. See. e.g., U.S. Pat. Nos. 7,910,296; 7,901,880; and 7,459,274. In some embodiments, amplification can be performed using primers that are gene specific. Alternatively, adaptors can be added to the ends of the randomly fragmented DNA, the DNA can be digested with a methylation-dependent or methylation-sensitive restriction enzyme, intact DNA can be amplified using primers that hybridize to the adaptor sequences. In this case, a second step can be performed to determine the presence, absence or quantity of a particular gene in an amplified pool of DNA. In some embodiments, the DNA is amplified using real-time, quantitative PCR.

In other embodiments, the methods comprise quantifying the average methylation density in a target sequence within a population of genomic DNA. In some embodiments, the method comprises contacting genomic DNA with a methylation-dependent restriction enzyme or methylation-sensitive restriction enzyme under conditions that allow for at least some copies of potential restriction enzyme cleavage sites in the locus to remain uncleaved; quantifying intact copies of the locus; and comparing the quantity of amplified product to a control value representing the quantity of methylation of control DNA, thereby quantifying the average methylation density in the locus compared to the methylation density of the control DNA.

The quantity of methylation of a locus of DNA can be determined by providing a sample of genomic DNA comprising the locus, cleaving the DNA with a restriction enzyme that is either methylation-sensitive or methylation-dependent, and then quantifying the amount of intact DNA or quantifying the amount of cut DNA at the DNA locus of interest. The amount of intact or cut DNA will depend on the initial amount of genomic DNA containing the locus, the amount of methylation in the locus, and the number (i.e., the fraction) of nucleotides in the locus that are methylated in the genomic DNA. The amount of methylation in a DNA locus can be determined by comparing the quantity of intact DNA or cut DNA to a control value representing the quantity of intact DNA or cut DNA in a similarly-treated DNA sample. The control value can represent a known or predicted number of methylated nucleotides. Alternatively, the control value can represent the quantity of intact or cut DNA from the same locus in another (e.g., normal, non-diseased) cell or a second locus.

By using at least one methylation-sensitive or methylation-dependent restriction enzyme under conditions that allow for at least some copies of potential restriction enzyme cleavage sites in the locus to remain uncleaved and subsequently quantifying the remaining intact copies and comparing the quantity to a control, average methylation density of a locus can be determined. If the methylation-sensitive restriction enzyme is contacted to copies of a DNA locus under conditions that allow for at least some copies of potential restriction enzyme cleavage sites in the locus to remain uncleaved, then the remaining intact DNA will be directly proportional to the methylation density, and thus may be compared to a control to determine the relative methylation density of the locus in the sample. Similarly, if a methylation-dependent restriction enzyme is contacted to copies of a DNA locus under conditions that allow for at least some copies of potential restriction enzyme cleavage sites in the locus to remain uncleaved, then the remaining intact DNA will be inversely proportional to the methylation density, and thus may be compared to a control to determine the relative methylation density of the locus in the sample. Such assays are disclosed in, e.g., U.S. Pat. No. 7,910,296.

Quantitative amplification methods (e.g., quantitative PCR or quantitative linear amplification) can be used to quantify the amount of intact DNA within a locus flanked by amplification primers following restriction digestion. Methods of quantitative amplification are disclosed in, e.g., U.S.

Pat. Nos. 6,180,349; 6,033,854; and 5,972,602, as well as in, e.g., DeGraves, et al., 34(1) BIOTECHNIQUES 106-15 (2003); Deiman B, et al., 20(2) MOL. BIOTECHNOL. 163-79 (2002); and Gibson et al., 6 GENOME RESEARCH 995-1001 (1996). Amplifications may be monitored in "real time."

Additional methods for detecting DNA methylation can involve genomic sequencing before and after treatment of the DNA with bisulfite. See, e.g., Frommer et al., 89 PROC. NATL. ACAD. SCI. USA 1827-31 (1992). When sodium bisulfite is contacted to DNA, unmethylated cytosine is converted to uracil, while methylated cytosine is not modified. In some embodiments, restriction enzyme digestion of PCR products amplified from bisulfite-converted DNA is used to detect DNA methylation. See. e.g., Xiong & Laird, 25 NUCLEIC ACIDS RES. 2532-34 (1997); and Sadri & Homsby, 24 NUCL. ACIDS RES. 5058-59 (1996).

In some embodiments, a MethyLight assay is used alone or in combination with other methods to detect DNA methylation. See, Eads et al., 59 CANCER RES. 2302-06 (1999). Briefly, in the MethyLight process genomic DNA is converted in a sodium bisulfite reaction (the bisulfite process converts unmethylated cytosine residues to uracil). Amplification of a DNA sequence of interest is then performed using PCR primers that hybridize to CpG dinucleotides. By using primers that hybridize only to sequences resulting from bisulfite conversion of unmethylated DNA, (or alternatively to methylated sequences that are not converted) amplification can indicate methylation status of sequences where the primers hybridize. Similarly, the amplification product can be detected with a probe that specifically binds to a sequence resulting from bisulfite treatment of a unmethylated (or methylated) DNA. If desired, both primers and probes can be used to detect methylation status. Thus, kits for use with MethyLight can include sodium bisulfite as well as primers or detectably-labeled probes (including but not limited to Taqman or molecular beacon probes) that distinguish between methylated and unmethylated DNA that have been treated with bisulfite. Other kit components can include, e.g., reagents necessary for amplification of DNA including but not limited to, PCR buffers, deoxynucleotides; and a thermostable polymerase.

In other embodiments, a Methylation-sensitive Single Nucleotide Primer Extension (Ms-SNuPE) reaction is used alone or in combination with other methods to detect DNA methylation. See Gonzalgo & Jones, 25 NUCLEIC ACIDS RES. 2529-31 (1997). The Ms-SNuPE technique is a quantitative method for assessing methylation differences at specific CpG sites based on bisulfite treatment of DNA, followed by single-nucleotide primer extension. Briefly, genomic DNA is reacted with sodium bisulfite to convert unmethylated cytosine to uracil while leaving 5-methylcytosine unchanged. Amplification of the desired target sequence is then performed using PCR primers specific for bisulfite-converted DNA, and the resulting product is isolated and used as a template for methylation analysis at the CpG site(s) of interest. Typical reagents (e.g., as might be found in a typical Ms-SNuPE-based kit) for Ms-SNuPE analysis can include, but are not limited to: PCR primers for specific gene (or methylation-altered DNA sequence or CpG island); optimized PCR buffers and deoxynucleotides; gel extraction kit; positive control primers; Ms-SNuPE primers for a specific gene; reaction buffer (for the Ms-SNuPE reaction); and detectably-labeled nucleotides. Additionally, bisulfite conversion reagents may include: DNA denaturation buffer; sulfonation buffer; DNA recovery regents or kit (e.g., precipitation, ultrafiltration, affinity column); desulfonation buffer; and DNA recovery components.

In further embodiments, a methylation-specific PCR reaction is used alone or in combination with other methods to detect DNA methylation. A methylation-specific PCR assay entails initial modification of DNA by sodium bisulfite, converting all unmethylated, but not methylated, cytosines to uracil, and subsequent amplification with primers specific for methylated versus unmethylated DNA. See, Herman et al., 93 PROC. NATL. ACAD. SCI. USA 9821-26, (1996); and U.S. Pat. No. 5,786,146.

Additional methylation detection methods include, but are not limited to, methylated CpG island amplification (see, Toyota et al., 59 CANCER RES. 2307-12 (1999)) and those methods described in, e.g., U.S. Pat. Nos. 7,553,627; 6,331,393; U.S. patent Ser. No. 12/476,981; U.S. Patent Publication No. 2005/0069879; Rein, et al., 26(10) NUCLEIC ACIDS RES. 2255-64 (1998); and Olek et al., 17(3) NAT. GENET. 275-6 (1997).

III. Determination of a Patient's PPD Status

The present invention relates to the use of biomarkers to detect or predict PPD. More specifically, the biomarkers of the present invention can be used in diagnostic tests to determine, qualify, and/or assess PPD status, for example, to diagnose or predict PPD, in an individual, subject or patient. More specifically, the biomarkers to be detected in diagnosing PPD include, but are not limited to, PBPC1L, HP1BP3 and TTC9B. Other biomarkers known in the relevant art may be used in combination with the biomarkers described herein including, but not limited to, the assessment of levels of hormones such as oxytocin, estrogen, progesterone, and their metabolites, questionnaires such as the Pregnancy Risk Questionnaire (PRQ; 18 antenatal items) and the Edinburgh Depression Scale, gene expression measures, or genetic variation deemed predictive of PPD.

A. Biomarker Panels

The biomarkers of the present invention can be used in diagnostic tests to assess, determine, and/or qualify (used interchangeably herein) PPD status in a patient. The phrase "PPD status" includes any distinguishable manifestation of the disease, including non-disease. For example, PPD status includes, without limitation, the presence or absence of PPD in a patient), the risk of developing PPD, the stage of PPD, the progress of PPD (e.g., progress of PPD over time) and the effectiveness or response to treatment of PPD (e.g., clinical follow up and surveillance of PPD after treatment). Based on this status, further procedures may be indicated, including additional diagnostic tests or therapeutic procedures or regimens.

The power of a diagnostic test to correctly predict status is commonly measured as the sensitivity of the assay, the specificity of the assay or the area under a receiver operated characteristic ("ROC") curve. Sensitivity is the percentage of true positives that are predicted by a test to be positive, while specificity is the percentage of true negatives that are predicted by a test to be negative. An ROC curve provides the sensitivity of a test as a function of 1-specificity. The greater the area under the ROC curve, the more powerful the predictive value of the test. Other useful measures of the utility of a test are positive predictive value and negative predictive value. Positive predictive value is the percentage of people who test positive that are actually positive. Negative predictive value is the percentage of people who test negative that are actually negative.

In particular embodiments, the biomarker panels of the present invention may show a statistical difference in different PPD statuses of at least $p<0.05$, $p<10^{-2}$, $p<10^{-3}$, $p<10^{-4}$ or $p<10^{-5}$. Diagnostic tests that use these biomarkers may show an ROC of at least 0.6, at least about 0.7, at least about 0.8, or at least about 0.9.

The biomarkers are differentially methylated in UI (or NC) and PPD, and, therefore, are useful in aiding in the determination of PPD status. In certain embodiments, the biomarkers are measured in a patient sample using the methods described herein and compared, for example, to predefined biomarker levels and correlated to PPD status. In particular embodiments, the measurement(s) may then be compared with a relevant diagnostic amount(s), cut-off(s), or multivariate model scores that distinguish a positive PPD status from a negative PPD status. The diagnostic amount(s) represents a measured amount of a hypermethylated biomarker(s) above which or below which a patient is classified as having a particular PPD status. For example, if the biomarker(s) is/are hypermethylated compared to normal during PPD, then a measured amount(s) above the diagnostic cutoff(s) provides a diagnosis of PPD. Alternatively, if the biomarker(s) is/are hypomethylated in a patient, then a measured amount(s) at or below the diagnostic cutoff(s) provides a diagnosis of non-PPD. As is well understood in the art, by adjusting the particular diagnostic cut-off(s) used in an assay, one can increase sensitivity or specificity of the diagnostic assay depending on the preference of the diagnostician. In particular embodiments, the particular diagnostic cut-off can be determined, for example, by measuring the amount of biomarker hypermethylation in a statistically significant number of samples from patients with the different PPD statuses, and drawing the cut-off to suit the desired levels of specificity and sensitivity.

Indeed, as the skilled artisan will appreciate there are many ways to use the measurements of the methylation status of two or more biomarkers in order to improve the diagnostic question under investigation. In a quite simple, but nonetheless often effective approach, a positive result is assumed if a sample is hypermethylation positive for at least one of the markers investigated.

Furthermore, in certain embodiments, the methylation values measured for markers of a biomarker panel are mathematically combined and the combined value is correlated to the underlying diagnostic question. Methylated biomarker values may be combined by any appropriate state of the art mathematical method. Well-known mathematical methods for correlating a marker combination to a disease status employ methods like discriminant analysis (DA) (e.g., linear-, quadratic-, regularized-DA), Discriminant Functional Analysis (DFA), Kernel Methods (e.g., SVM), Multidimensional Scaling (MDS), Nonparametric Methods (e.g., k-Nearest-Neighbor Classifiers), PLS (Partial Least Squares), Tree-Based Methods (e.g., Logic Regression, CART, Random Forest Methods, Boosting/Bagging Methods), Generalized Linear Models (e.g., Logistic Regression), Principal Components based Methods (e.g., SIMCA), Generalized Additive Models, Fuzzy Logic based Methods, Neural Networks and Genetic Algorithms based Methods. The skilled artisan will have no problem in selecting an appropriate method to evaluate a biomarker combination of the present invention. In one embodiment, the method used in a correlating methylation status of a biomarker combination of the present invention, e.g. to diagnose PPD, is selected from DA (e.g., Linear-, Quadratic-, Regularized Discriminant Analysis), DFA, Kernel Methods (e.g., SVM), MDS, Nonparametric Methods (e.g., k-Nearest-Neighbor Classifiers), PLS (Partial Least Squares), Tree-Based Methods (e.g., Logic Regression, CART, Random Forest Methods, Boosting Methods), or Generalized Linear Models (e.g., Logistic Regression), and Principal Components Analysis. Details relating to these statistical methods are found in the following references: Ruczinski et al., 12 J. of Computational and Graphical Statistics 475-511 (2003); Friedman, J. H., 84 J. of the American Statistical Association 165-75 (1989); Hastie, Trevor, Tibshirani, Robert, Friedman, Jerome, The Elements of Statistical Learning, Springer Series in Statistics (2001); Breiman, L., Friedman, J. H., Olshen, R. A., Stone, C. J. Classification and regression trees, California: Wadsworth (1984); Breiman, L., 45 Machine Learning 5-32 (2001); Pepe, M. S., The Statistical Evaluation of Medical Tests for Classification and Prediction, Oxford Statistical Science Series, 28 (2003); and Duda, R. O., Hart, P. E., Stork, D. G., Pattern Classification, Wiley Interscience, 2nd Edition (2001).

B. Determining Risk of Developing PPD

In a specific embodiment, the present invention provides methods for determining the risk of developing PPD in a patient. Biomarker methylation percentages, amounts or patterns are characteristic of various risk states, e.g., high, medium or low. The risk of developing PPD is determined by measuring the methylation status of the relevant biomarkers and then either submitting them to a classification algorithm or comparing them with a reference amount, i.e., a predefined level or pattern of methylated (and/or unmethylated) biomarkers that is associated with the particular risk level.

C. Determining PPD Severity

In another embodiment, the present invention provides methods for determining the severity of PPD in a patient. A particular stage or severity of PPD may have a characteristic level of hypermethylation of a biomarker or relative hypermethylated levels of a set of biomarkers (a pattern). The severity of PPD can be determined by measuring the methylation status of the relevant biomarkers and then either submitting them to a classification algorithm or comparing them with a reference amount, i.e., a predefined methylation level or pattern of methylated biomarkers that is associated with the particular stage.

D. Determining PPD Prognosis

In one embodiment, the present invention provides methods for determining the course of PPD in a patient. PPD course refers to changes in PPD status over time, including PPD progression (worsening) and PPD regression (improvement). Over time, the amount or relative amount (e.g., the pattern) of hypermethylation of the biomarkers changes. For example, hypermethylation of biomarker "X" and "Y" may be increased with PPD. Therefore, the trend of these biomarkers, either increased or decreased methylation over time toward PPD or non-PPD indicates the course of the disease. Accordingly, this method involves measuring the methylation level or status of one or more biomarkers in a patient at least two different time points, e.g., a first time and a second time, and comparing the change, if any. The course of PPD is determined based on these comparisons.

E. Patient Management

In certain embodiments of the methods of qualifying PPD status, the methods further comprise managing patient treatment based on the status. Such management includes the actions of the physician or clinician subsequent to determining PPD status. For example, if a physician makes a diagnosis or prognosis of PPD, then a certain regime of monitoring would follow. An assessment of the course of PPD using the methods of the present invention may then require a certain PPD therapy regimen. Alternatively, a diagnosis of non-PPD might be followed with further testing to determine a specific disease that the patient might be suffering from. Also, further tests may be called for if the diagnostic test gives an inconclusive result on PPD status.

F. Determining Therapeutic Efficacy of Pharmaceutical Drug

In another embodiment, the present invention provides methods for determining the therapeutic efficacy of a pharmaceutical drug. These methods are useful in performing clinical trials of the drug, as well as monitoring the progress of a patient on the drug. Therapy or clinical trials involve administering the drug in a particular regimen. The regimen may involve a single dose of the drug or multiple doses of the drug over time. The doctor or clinical researcher monitors the effect of the drug on the patient or subject over the course of administration. If the drug has a pharmacological impact on the condition, the amounts or relative amounts (e.g., the pattern or profile) of hypermethylation of one or more of the biomarkers of the present invention may change toward a non-PPD profile. Therefore, one can follow the course of the methylation status of one or more biomarkers in the patient during the course of treatment. Accordingly, this method involves measuring methylation levels of one or more biomarkers in a patient receiving drug therapy, and correlating the levels with the PPD status of the patient (e.g., by comparison to predefined methylation levels of the biomarkers that correspond to different PPD statuses). One embodiment of this method involves determining the methylation levels of one or more biomarkers at at least two different time points during a course of drug therapy, e.g., a first time and a second time, and comparing the change in methylation levels of the biomarkers, if any. For example, the methylation levels of one or more biomarkers can be measured before and after drug administration or at two different time points during drug administration. The effect of therapy is determined based on these comparisons. If a treatment is effective, then the methylation status of one or more biomarkers will trend toward normal, while if treatment is ineffective, the methylation status of one or more biomarkers will trend toward PPD indications.

G. Generation of Classification Algorithms for Qualifying PPD Status

In some embodiments, data that are generated using samples such as "known samples" can then be used to "train" a classification model. A "known sample" is a sample that has been pre-classified. The data that are used to form the classification model can be referred to as a "training data set." The training data set that is used to form the classification model may comprise raw data or pre-processed data. Once trained, the classification model can recognize patterns in data generated using unknown samples. The classification model can then be used to classify the unknown samples into classes. This can be useful, for example, in predicting whether or not a particular biological sample is associated with a certain biological condition (e.g., diseased versus non-diseased).

Classification models can be formed using any suitable statistical classification or learning method that attempts to segregate bodies of data into classes based on objective parameters present in the data. Classification methods may be either supervised or unsupervised. Examples of supervised and unsupervised classification processes are described in Jain, "Statistical Pattern Recognition: A Review", IEEE Transactions on Pattern Analysis and Machine Intelligence, Vol. 22, No. 1, January 2000, the teachings of which are incorporated by reference.

In supervised classification, training data containing examples of known categories are presented to a learning mechanism, which learns one or more sets of relationships that define each of the known classes. New data may then be applied to the learning mechanism, which then classifies the new data using the learned relationships. Examples of supervised classification processes include linear regression processes (e.g., multiple linear regression (MLR), partial least squares (PLS) regression and principal components regression (PCR)), binary decision trees (e.g., recursive partitioning processes such as CART), artificial neural networks such as back propagation networks, discriminant analyses (e.g., Bayesian classifier or Fischer analysis), logistic classifiers, and support vector classifiers (support vector machines).

Another supervised classification method is a recursive partitioning process. Recursive partitioning processes use recursive partitioning trees to classify data derived from unknown samples. Further details about recursive partitioning processes are provided in U.S. Patent Application No. 2002 0138208 A1 to Paulse et al., "Method for analyzing mass spectra."

In other embodiments, the classification models that are created can be formed using unsupervised learning methods. Unsupervised classification attempts to learn classifications based on similarities in the training data set, without pre-classifying the spectra from which the training data set was derived. Unsupervised learning methods include cluster analyses. A cluster analysis attempts to divide the data into "clusters" or groups that ideally should have members that are very similar to each other, and very dissimilar to members of other clusters. Similarity is then measured using some distance metric, which measures the distance between data items, and clusters together data items that are closer to each other. Clustering techniques include the MacQueen's K-means algorithm and the Kohonen's Self-Organizing Map algorithm.

Learning algorithms asserted for use in classifying biological information are described, for example, in PCT International Publication No. WO 01/31580 (Barnhill et al., "Methods and devices for identifying patterns in biological systems and methods of use thereof"), U.S. Patent Application Publication No. 2002/0193950 (Gavin et al. "Method or analyzing mass spectra"), U.S. Patent Application Publication No. 2003/0004402 (Hitt et al., "Process for discriminating between biological states based on hidden patterns from biological data"), and U.S. Patent Application Publication No. 2003/0055615 (Zhang and Zhang, "Systems and methods for processing biological expression data").

The classification models can be formed on and used on any suitable digital computer. Suitable digital computers include micro, mini, or large computers using any standard or specialized operating system, such as a Unix, Windows® or Linux™ based operating system. In embodiments utilizing a mass spectrometer, the digital computer that is used may be physically separate from the mass spectrometer that is used to create the spectra of interest, or it may be coupled to the mass spectrometer.

The training data set and the classification models according to embodiments of the invention can be embodied by computer code that is executed or used by a digital computer. The computer code can be stored on any suitable computer readable media including optical or magnetic disks, sticks, tapes, etc., and can be written in any suitable computer programming language including R, C, C++, visual basic, etc.

The learning algorithms described above are useful both for developing classification algorithms for the biomarker biomarkers already discovered, and for finding new biomarker biomarkers. The classification algorithms, in turn, form the base for diagnostic tests by providing diagnostic values (e.g., cut-off points) for biomarkers used singly or in combination.

H. Kits for the Detection of PPD Biomarker Biomarkers

In another aspect, the present invention provides kits for qualifying PPD status, which kits are used to detect or measure the methylation status/levels of the biomarkers described herein. Such kits can comprise at least one polynucleotide that hybridizes to at least one of the diagnostic biomarker sequences of the present invention and at least one reagent for detection of gene methylation. Reagents for detection of methylation include, e.g., sodium bisulfite, polynucleotides designed to hybridize to a sequence that is the product of a biomarker sequence of the invention if the biomarker sequence is not methylated (e.g., containing at least one C→U conversion), and/or a methylation-sensitive or methylation-dependent restriction enzyme. The kits can further provide solid supports in the form of an assay apparatus that is adapted to use in the assay. The kits may further comprise detectable labels, optionally linked to a polynucleotide, e.g., a probe, in the kit. Other materials useful in the performance of the assays can also be included in the kits, including test tubes, transfer pipettes, and the like. The kits can also include written instructions for the use of one or more of these reagents in any of the assays described herein.

In some embodiments, the kits of the invention comprise one or more (e.g., 1, 2, 3, 4, or more) different polynucleotides (e.g., primers and/or probes) capable of specifically amplifying at least a portion of a DNA region of a biomarker of the present invention including HP1BP3 and TTC9B. Optionally, one or more detectably-labeled polypeptides capable of hybridizing to the amplified portion can also be included in the kit. In some embodiments, the kits comprise sufficient primers to amplify 2, 3, 4, 5, 6, 7, 8, 9, 10, or more different DNA regions or portions thereof, and optionally include detectably-labeled polynucleotides capable of hybridizing to each amplified DNA region or portion thereof. The kits further can comprise a methylation-dependent or methylation sensitive restriction enzyme and/or sodium bisulfite.

In some embodiments, the kits comprise sodium bisulfite, primers and adapters (e.g., oligonucleotides that can be ligated or otherwise linked to genomic fragments) for whole genome amplification, and polynucleotides (e.g., detectably-labeled polynucleotides) to quantify the presence of the converted methylated and or the converted unmethylated sequence of at least one cytosine from a DNA region of a biomarker of the present invention including HP1BP3 and TTC9B.

In some embodiments, the kits comprise methylation sensing restriction enzymes (e.g., a methylation-dependent restriction enzyme and/or a methylation-sensitive restriction enzyme), primers and adapters for whole genome amplification, and polynucleotides to quantify the number of copies of at least a portion of a DNA region of a biomarker of the present invention including HP1BP3 and TTC9B.

In some embodiments, the kits comprise a methylation binding moiety and one or more polynucleotides to quantify the number of copies of at least a portion of a DNA region of a biomarker of the present invention including HP1BP3 and TTC9B. A methylation binding moiety refers to a molecule (e.g., a polypeptide) that specifically binds to methylcytosine. Examples include restriction enzymes or fragments thereof that lack DNA cutting activity but retain the ability to bind methylated DNA, antibodies that specifically bind to methylated DNA, etc.).

Without further elaboration, it is believed that one skilled in the art, using the preceding description, can utilize the present invention to the fullest extent. The following examples are illustrative only, and not limiting of the remainder of the disclosure in any way whatsoever.

EXAMPLES

The following examples are put forth so as to provide those of ordinary skill in the art with a complete disclosure and description of how the compounds, compositions, articles, devices, and/or methods described and claimed herein are made and evaluated, and are intended to be purely illustrative and are not intended to limit the scope of what the inventors regard as their invention. Efforts have been made to ensure accuracy with respect to numbers (e.g., amounts, temperature, etc.) but some errors and deviations should be accounted for herein. Unless indicated otherwise, parts are parts by weight, temperature is in degrees Celsius or is at ambient temperature, and pressure is at or near atmospheric. There are numerous variations and combinations of reaction conditions, e.g., component concentrations, desired solvents, solvent mixtures, temperatures, pressures and other reaction ranges and conditions that can be used to optimize the product purity and yield obtained from the described process. Only reasonable and routine experimentation will be required to optimize such process conditions.

Materials and Methods

Figure 4B:
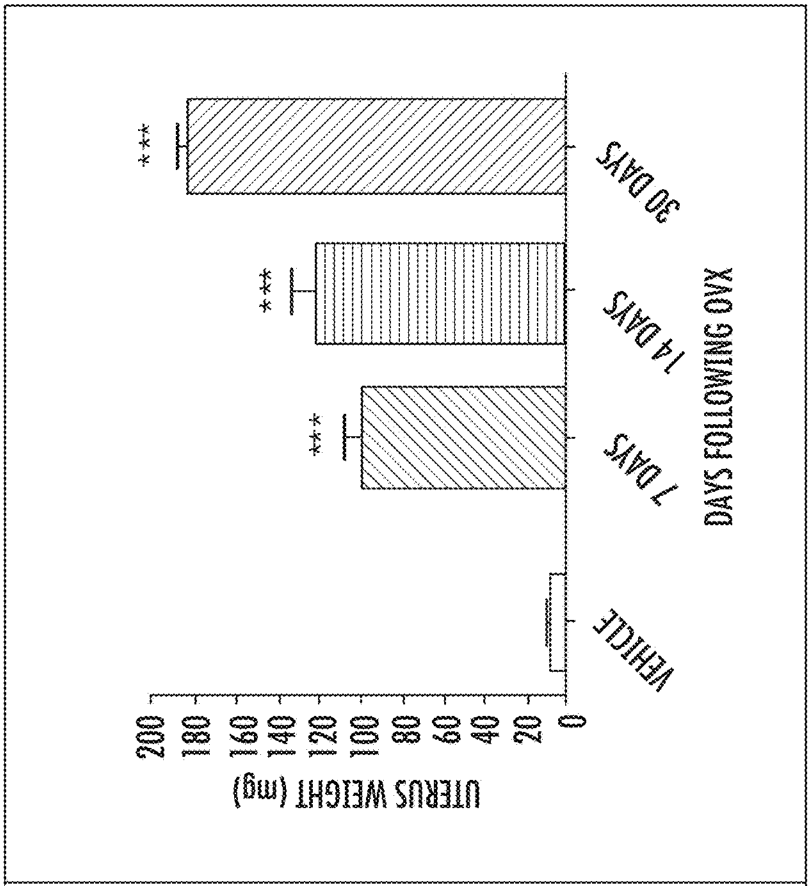
FIG. 4A-4B. Serum E2 and uterus weights of experimental mice. E2 levels (FIG. 4A) and uterus weights (FIG. B) at 1, 2, and 4 weeks in siliastic tube implanted OVX mice receiving E2 or vehicle. Analysis of serum demonstrated consistent levels of estradiol in the blood and at 1, 2, and 4 weeks, which consistent with the literature was predictive of an increase in uterus weight over those time points. ***$p<0.001$ vs. vehicle (empty capsule).
Figure 4A:
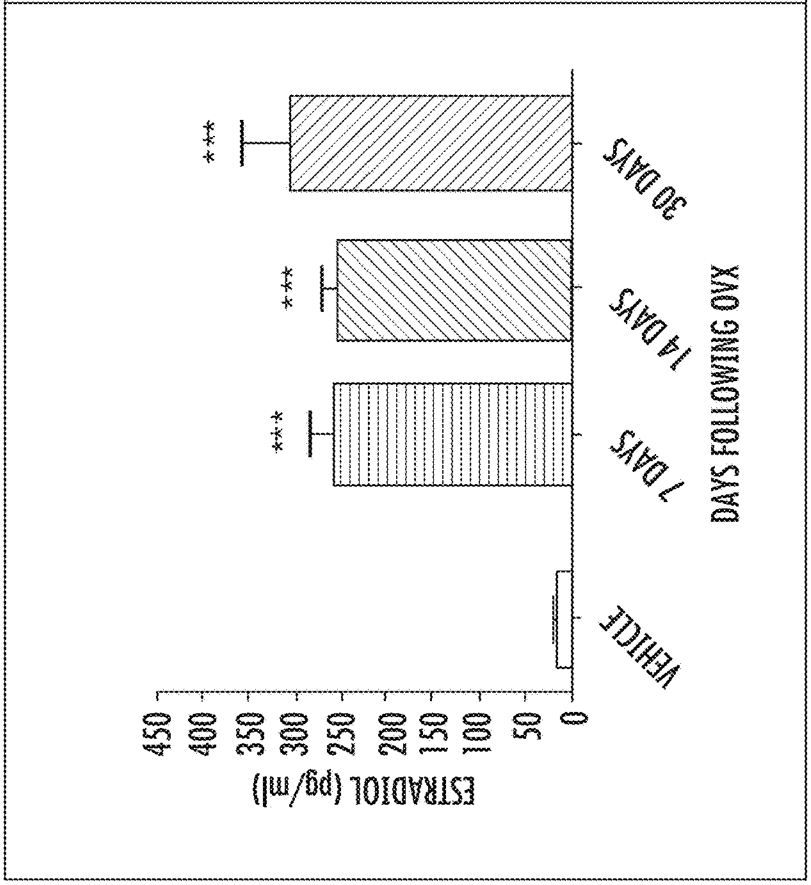

Experimental Animals. C57BL/6J mice were ovariectomized at eight weeks of age. At the time of surgery mice were randomized to receive (s.c. implantation) a Silastic™ capsule (i.d. 1.02 mm; o.d. 2.16 mm) containing 5 mm of dry packed 17β-estradiol (n=5/group/timepoint). Controls received an empty capsule. Analysis of serum demonstrated consistent levels of estradiol in the blood and at 1, 2, and 4 weeks, which was predictive of an increase in uterus weight over those time points (FIG. 4).

Affymetrix DNA Methylation Profiling. DNA methylation was assessed in mice using methods described previously[13, 14] using HpaII and HinPII enzymes. Following quality control assessment through Agilent BioAnalyzer based visualization, the unmethylated fraction of genomic DNA was hybridized to Affymetrix GeneChip® Mouse Tiling Promoter 1.0R Arrays at the JHMI Deep Sequencing and Microarray Core facility. Affymetrix cell files were background corrected and quantile normalized using the AffyTiling package in R, yielding normalized log 2 transformed M values representative of the DNA hypomethylation profile per sample. DMRs were calculated using the BioTile algorithm (http://psychiatry.igm.jhmi.edu/kaminsky/software.htn). Identified DMRs were refined by filtering out those not flanked within 1 kb of the DMR boundary by either a HpaI or HinPII restriction site based on the mouse mm8 genome build sequence. Microarray data is located under GEO accession: GSE43460.

Human Sample. We recruited 93 pregnant women with a history of either Major Depression or Bipolar Disorder (I, II or NOS) and prospectively followed them during pregnancy and after delivery in order to identify genetic and clinical characteristics that precede the development of a postpartum depressive episode. Approximately one-third of the sample had Bipolar Disorder. The average age of the participants was 30.6 and 70% of the sample was Caucasian. Participants were managed by their treating psychiatrist as clinically indicated and were evaluated during each trimester of pregnancy and then 1 week, 1 month and 3 months postpartum. Women were classified as being depressed if they met DSM-IV criteria for a Major Depressive Episode (MDE) based on a psychiatric interview at each time point (first, second, and third trimester and 1 week and 1 month postpartum). We analyzed a subgroup of 32 women euthymic during the third trimester (prepartum euthymic), 34.4% of this subsample (N=11) became depressed within the first 4 weeks postpartum and met DSM-IV criteria for MDE. A second subgroup of 19 women depressed during pregnancy (prepartum depressed) was assessed in subsequent analyses as an independent replication cohort, of which N=12 remained depressed within the first 4 weeks postpartum and met DSM-IV criteria for MDE. The trimester of blood draw is depicted in Table 3.

TABLE 3

Clinical sample collection data

| | Trimester | | | |
|---|---|---|---|---|
| | 1st | 2nd | 3rd | Total |
| Mood Status Prepartum: Post Partum | | | | |
| Euthymic: PPD | 2 | 7 | 4 | 13 |
| Euthymic: non-PPD | 7 | 8 | 7 | 22 |
| Replication Sample | | | | |
| Depressed: PPD | 1 | 6 | 5 | 12 |
| Depressed: non-PPD | 1 | 2 | 4 | 7 |

Illumina DNA Methylation Profiling. Samples quality assessment and microarray analysis were conducted at The Sidney Kimmel Cancer Center Microarray Core Facility at Johns Hopkins University using Illumina's Infinium Human Methylation450 Beadchip Kit (WG-314-1001) according to the manufacturer's manual. Images were processed in Illumina's iScan scanner and data were extracted using Methylation Module of GenomeStudio v1.0 Software. Illumina probe type was corrected using the Beta2M function in the watermelon package in R. Methylation status of each CpG site was calculated as β (beta) value based on following definition:

$$\beta\text{ value}=(\text{signal intensity of methylation-detection probe})/(\text{signal intensity of methylation-detection probe}+\text{signal intensity of non-methylation-detection probe}+100).$$

Microarray data is located under GEO accession: GSE44132.

Cell Sub-Type Analysis. We quantified cell sub-fraction percentages for CD8 T cells, CD4 T cells, B cells, monocytes, and granulocytes by inputting DNA methylation signatures of 473 loci into an algorithm designed for quantification of the above cell-types using DNA methylation proxies from HM450 arrays[15]. Prior to cell-type proportion calculation for the prepartum depressed cohort, DNA methylation values at the 473 loci were transformed by subtracting the residuals from a linear model of the mean DNA methylation values of three cross batch controls from the prepartum euthymic cohort (batch 1) vs. the mean DNA methylation values from two replicates of the same sample run in the prepartum depressed cohort (batch 2).

Sodium Bisulfite Pyrosequencing. Bisulfite conversion was carried out using EZ DNA Methylation Gold Kit (Zymo Research) according to the manufacturer's instructions. Nested PCR amplifications were performed with a standard PCR protocol in 25 ml volume reactions containing 3-4 μl of sodium-bisulfite-treated DNA, 0.2 uM primers, and master mix containing Taq DNA polymerase (Sigma Aldrich). Primer sequences can be found in Table 4. PCR amplicons were processed for pyrosequencing analysis according to the manufacturer's standard protocol (Qiagen) using a PyroMark MD system (QIAGEN) with Pyro Q-CpG 1.0.9 software (QIAGEN) for CpG methylation quantification.

TABLE 4

Primer Sequences

| Gene | Primer Name | Primer Sequence (5'-3') |
|---|---|---|
| PABPC1L | PABPC1L_F_out | TTTGGTGTAATGGATGTGTAATG (SEQ ID NO: 1) |
| | PABPC1L_R_out | AAACCTTCAACCTAACCTTAAAC (SEQ ID NO: 2) |
| | PABPC1L_F_in | biotin-TATGAGTTAGTATTAAGAAAGGTTTTAGT (SEQ ID NO: 3) |
| | PABPC1L_R_in | AAACTCTCAAAACCCCCAACTCT (SEQ ID NO: 4) |
| | PABPC1L_Pyro1 | CAAAAAACCTAATCCAATCCCAC (SEQ ID NO: 5) |
| | PABPC1L_Pyro2 | AAACAAATAATCATCTTTCTAAACC (SEQ ID NO: 6) |
| | PABPC1L_Pyro3 | CTCCTAACAAAAATAAAAAAAAACCCAAACC (SEQ ID NO: 7) |
| HP1BP3 | HP1BP3_F_out | ATTTTTTTAAATTAGTTTTGAAGAGTTGTA (SEQ ID NO: 8) |
| | HP1BP3_R_out | CCTAAAAAAAAAATCCACCAAAAAAAC (SEQ ID NO: 9) |
| | HP1BP3_F_in | TTTTTTTGTATGTGAGGATTAGGGAG (SEQ ID NO: 10) |
| | HP1BP3_R_in | biotin-CAATCCCTTCTCTTAACTAAATTTCC (SEQ ID NO: 11) |
| | HP1BP3_Pyro1 | TTAAAAAAAGGTTTGTTTTTGAGTTG (SEQ ID NO: 12) |
| TTC9B | TTC9B_F_out | GGGGGAAAGAGTAGGAAGATA (SEQ ID NO: 13) |
| | TTC9B_R_out | AAACTAATCTCAAACTTCTAACCTC (SEQ ID NO: 14) |
| | TTC9B_F_in | biotin-TATTTTTTTATTAGTGGTATGATTTAGATAGT (SEQ ID NO: 15) |
| | TTC9B_R_in | CCTAAAAATAATATTATTATACCATATTACTAAT (SEQ ID NO: 16) |
| | TTC9B_Pyro1 | TTATTAGTGGTATGATTTAGATAGT (SEQ ID NO: 17) |
| OXTR | OXTR_F_out | GGGAGGTGATTTGGTTTTAGATT (SEQ ID NO: 18) |
| | OXTR_R_out | AAACTCCACTCCTAAAAACTCCA (SEQ ID NO: 19) |
| | OXTR_F_in | TATTTGTAGTGGTTTAGAGGAGGTA (SEQ ID NO: 20) |
| | OXTR_R_in | Biotin-TACTAAATCCACCCTAAAACAAACC (SEQ ID NO: 21) |
| | OXTR_Pyro1 | GAGTTGGGTTTTTGGGAATGGGATAAGTA (SEQ ID NO: 22) |

Statistical Analysis. All statistical tests were performed in R (http://wwiv.r-project.org/). Using an Anderson-Darling test from the nortest package, all distributions of data that rejected the null hypothesis of normality were subsequently evaluated with non-parametric tests. All statistical tests performed were two tailed and a $p<0.05$ is considered significant. Unless otherwise specified±denotes the standard error of the mean.

Weighted Genome Co-expression Network Analysis. Weighted Genome Co-expression Network Analysis (WGCNA)[16] was performed using the WGCNA package in K. In the mouse comparisons, 3,606 mean DMR values were used with a power of 20 and minimum module size of 10. For all human analyses, 13,091 nominally significant loci in the combined comparison of PPD (N=11) to non-PPD (N=21) euthymic cohort women were used for correlation with a power of 10 and minimum module size of 10.

Results

Figures 5A, 5B:
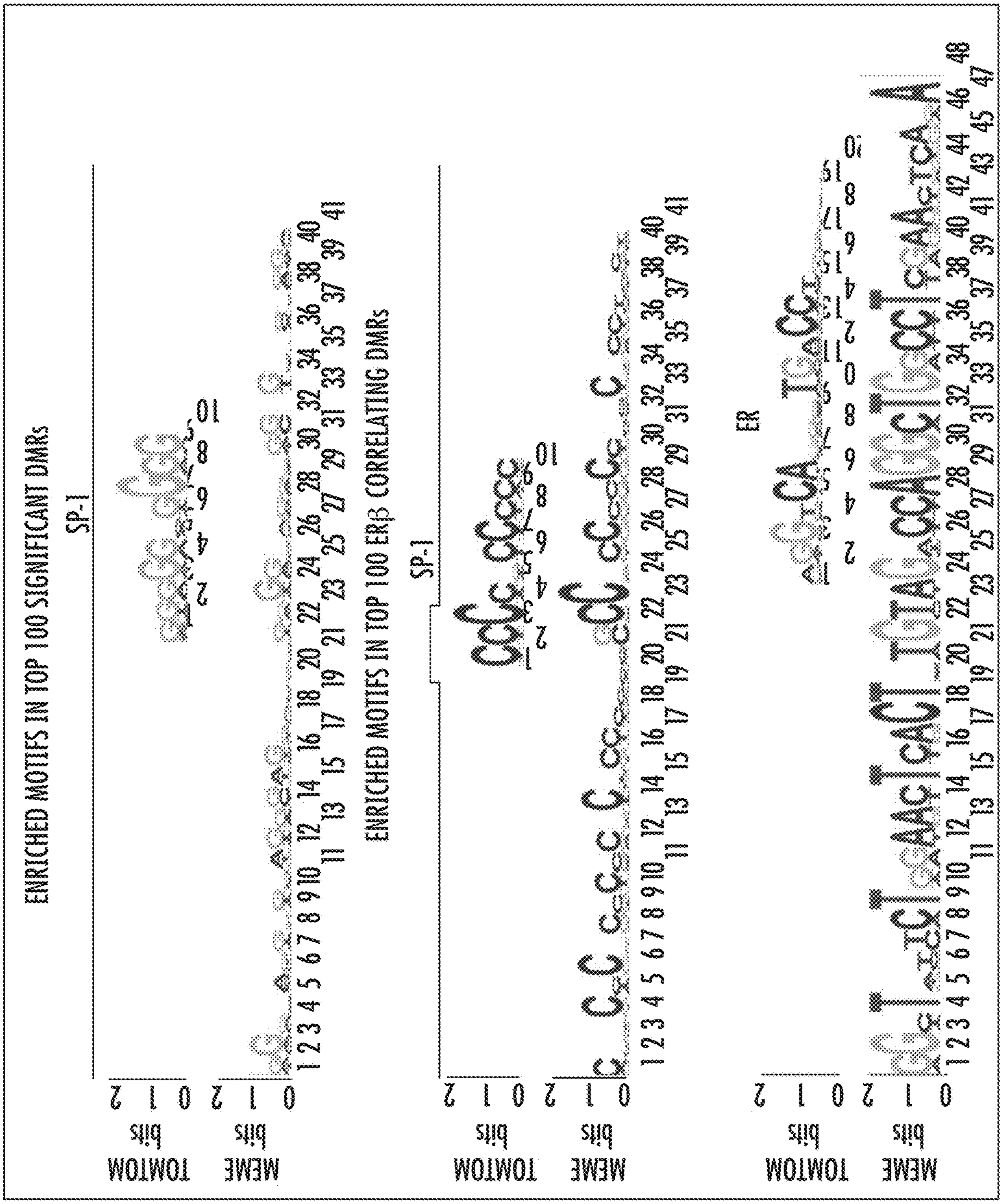
FIG. 5A-5B. Hippocampal E2 DMR enriched motifs.

Example 1: Identification of Hippocampal Targets of E2 Mediated DNA Methylation Change. We sought to identify hippocampal differentially methylated regions (DMRs) in the mouse associated with E2 exposure in order to model the molecular changes occurring during heightened estrogen levels in pregnancy. We chose to utilize hippocampal tissue because effects of E2 on mood are believed, in part, to be localized to the hippocampus, based on numerous studies including knock out experiments[17], 17β-estradiol (E2) administration experiments[18], and selective estrogen receptor (ER) antagonists and agonists[19-21] that demonstrate anxiolytic and antidepressant effects of E2 exposure in rodents. Furthermore in rodent models E2 administration has been shown to increase synaptic plasticity and dendritic spine density within the hippocampus[22, 23] while withdrawal from pregnancy levels of E2 results in decreased hippocampal BDNF expression[24] and suppressed hippocampal neurogenesis[25]. We identified 891 significant DMRs before correction for multiple testing. Of these, 380 DMRs exhibited a decrease and 511 exhibited an increase in DNA methylation in response to E2 (FIG. 1, Table 5). Gene ontology analysis using GOstat[26] identified a number of significantly enriched GO categories within genes proximal to the identified DMRs (Table 1). Motif enrichment analysis of genomic sequences of the top 100 significant E2 DMRs as well as ERβ promoter methylation correlated regions identified an enrichment for the SP-1 and ER transcription factor binding motifs (FIG. 5).

TABLE 1

Over-represented Gene Ontology Categories in E2 responsive DMRs

| GO category | N Identified | N in group | Corrected P value | Category |
|---|---|---|---|---|
| Methylation Decrease | | | | |
| GO: 0001505 | 10 | 88 | 0.005 | synaptic transmission: regulation of neurotransmitter levels |
| GO: 0003001 | 9 | 87 | 0.020 | generation of a signal involved in cell-cell signaling |
| GO: 0007267 | 17 | 325 | 0.027 | cell-cell signaling |
| GO: 0051640 | 5 | 27 | 0.037 | organelle localization |
| GO: 0045941 | 15 | 281 | 0.041 | positive regulation of nucleobase |
| Methylation Increase | | | | |
| GO: 0043231 | 144 | 6207 | $8.6 \times 10^{-5}$ | intracellular membrane-bound organelle |
| GO: 0005622 | 187 | 8708 | $8.6 \times 10^{-5}$ | intracellular |
| GO: 0043227 | 144 | 6212 | $8.6 \times 10^{-5}$ | membrane-bound organelle |
| GO: 0005737 | 126 | 5314 | $2.0 \times 10^{-4}$ | cytoplasm |
| GO: 0044424 | 179 | 8417 | $3.4 \times 10^{-4}$ | intracellular part |
| GO: 0043229 | 154 | 7027 | $5.9 \times 10^{-4}$ | intracellular organelle |
| GO: 0043226 | 154 | 7032 | $5.9 \times 10^{-4}$ | organelle |
| GO: 0016192 | 18 | 401 | $2.3 \times 10^{-3}$ | vesicle-mediated transport |
| GO: 0044444 | 78 | 3058 | $2.4 \times 10^{-3}$ | cytoplasmic part |
| GO: 0005794 | 22 | 552 | $3.0 \times 10^{-3}$ | Golgi apparatus |
| GO: 0005515 | 109 | 4751 | $4.6 \times 10^{-3}$ | protein binding |
| GO: 0043283 | 93 | 4055 | 0.020 | biopolymer metabolic process |

TABLE 5

| Cell-type differences across prepartum mood status and batch | | | | |
|---|---|---|---|---|
| Mood Status | Euthymic PP | Depressed PP | P value | Bonferroni P value |
| CD8 T | 40 + 0.048% | 38 + 0.098% | $1.2 \times 10^{-3}$ | $6.1 \times 10^{-3}$ |
| CD4 T | 9.9 + 0.088% | 7 + 0.12% | $2.7 \times 10^{-4}$ | $1.4 \times 10^{-3}$ |
| B cell | 2.9 + 0.048% | 1.3 + 0.06% | $1.5 \times 10^{-4}$ | $7.3 \times 10^{-4}$ |
| Monocyte | 2.8 + 0.032% | 1.7 + 0.042% | $1.1 \times 10^{-4}$ | $5.3 \times 10^{-4}$ |
| Granulocyte | 34 + 0.05% | 34 + 0.082% | 0.18 | 0.92 |
| Cross Batch | Batch1 Control (N = 3) | Batch 2 Control (N = 2) | P value | Bonferroni P value |
| CD8 T | 40 + 0.14% | 39 + 1.0% | 0.65 | 1.00 |
| CD4 T | 7.3 + 0.31% | 8.1 + 0.046% | 0.28 | 1.00 |
| B cell | 1.4 + 0.20% | 3 + 0.19% | 0.03 | 0.17 |
| Monocyte | 1.9 + 0.12% | 2.4 + 0.13% | 0.18 | 0.88 |
| Granulocyte | 36 + 0.12% | 33 + 0.39% | 0.09 | 0.45 |

Example 2: PPD DNA Methylation Differences are Correlated with E2 Mediated Epigenetic Change. We split the human sample into a discovery sample and replication sample consisting of N=6 and N=5 women who would and N=12 and N=9 who would not develop PPD, each with ~35% PPD to 65% non-PPD samples. In the discovery sample, we performed a probe wise student's t test between PPD and non-PPD cases. We cross referenced genomic locations of the E2 DMRs from the mouse data with syntenic loci located on the human microarray (FIG. 1B). Synteny was calculated based on the relative position of the implicated DMR (Mouse array) or individual CpG locus (Human array) from the closest proximal transcription start site within conserved sequence regions as established by the UCSC Genome Browser Liftover tool. Due to the nature of the enzymatic enrichment used in the mouse array experiment, a CpG locus was considered overlapping if it was adjacent within 200 bp of the implicated DMR. In total 1,578 human CpGs were located within the nominally significant mouse E2 DMRs. Pathway analysis of genes associated with overlapping loci using the g. Profiler analysis suite[27] identified a single significant GO category (GO: 0010646, frequency observed=0.19, expected=0.024, p=0.046) for 'regulation of cell communication' and an enrichment of SP-1 (M00196_4, frequency observed=0.51, expected=0.021, p=0.0084) and AP-2 (M00800_3, frequency observed=0.54, expected=0.021, p=0.0029) transcription factor binding motifs.

We next attempted to correlate the mean DNA methylation difference between PPD and non-PPD samples and E2 mediated DNA methylation fold change. No correlation was observed across the 1,578 overlapping loci (Spearman's Rho=−0.028, p=0.27). We refined the interrogated dataset to 103 loci exhibiting nominally significant association to PPD status and observed significant correlations in both the discovery sample (Spearman's Rho=0.21, p=0.030) and the replication sample (Spearman's Rho=0.2, p=0.042). The p value of association to PPD in the discovery sample was also correlated with E2 DMR effect size (Rho=−0.19, p=0.05) (FIG. 1C), suggesting that more robust PPD associations occur at targets of larger E2 mediated DNA methylation change. Furthermore, the mean PPD minus non-PPD value was significantly correlated across the discovery and replication cohorts (Spearman's Rho=0.32, p=0.0011) (FIG. 1D). Permutation testing (20,000 iterations) demonstrated that randomly selected groupings of 103 loci did not correlate better between cohorts ($p=5\times10^{5}$) nor with E2 DMR fold changes in either the discovery or replication samples (p=0.016 and p=0.02, respectively). This analysis suggests that the degree to which the discovery and replication cohorts agree is strongly influenced by their localization to syntenic regions of E2 mediated epigenetic reprogramming.

We evaluated the mean PPD minus non-PPD DNA methylation status at the nominally significant PPD associations in the prepartum depressed cohort (N=103 loci) and identified a trend for a positive correlation with the fold change at syntenic E2 DMRs (Spearman's Rho=0.19, p=0.054). A positive correlation of mean methylation difference between the 1,578 loci marked as E2 responsive was also observed between the prepartum depressed and euthymic cohorts (Spearman's Rho=0.078, p=0.002). Cumulatively, these results support our previous hypothesis that PPD risk may be mediated by an enhanced sensitivity to E2 mediated epigenetic reprogramming.

Figures 6A, 6B:
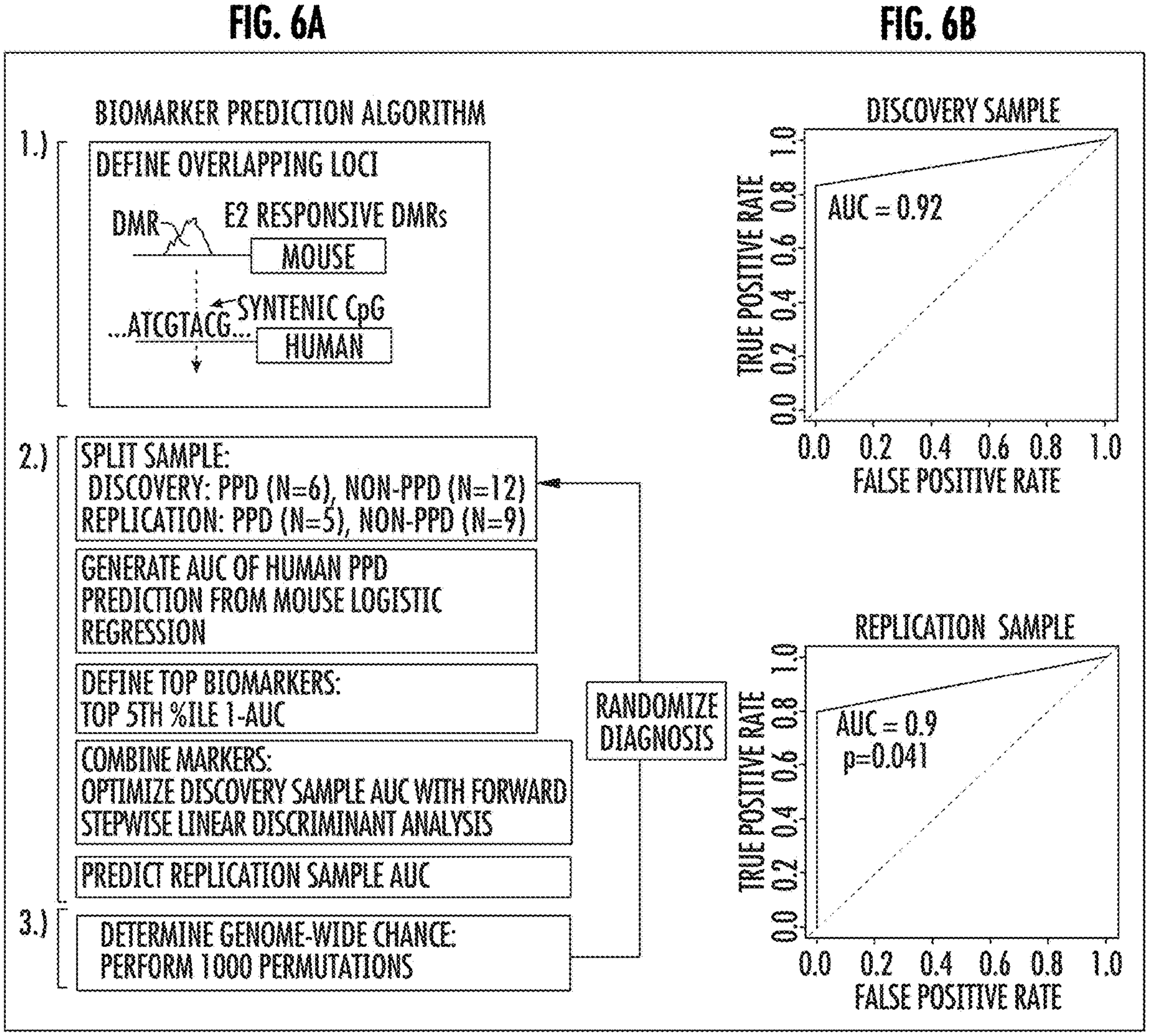
FIG. 6A-6B. Hippocampal E2 DMR enriched motifs.

Example 3: Identification of DNA Methylation Biomarkers Predictive of PPD. We next reasoned that if estrogen is important for PPD risk, we should be able to predict PPD status based on the degree to which E2 reprograms DNA methylation in the mouse. For each of the 1,578 mouse E2 DMRs that overlapped with the human dataset, we modeled the mean DNA methylation signature per DMR against the E2 treatment status. In a locus specific manner, we inputted the human DNA methylation levels per individual in the discovery sample and attempted to predict PPD status using logistic regression. For each locus, the AUC metric was used to measure prediction accuracy. We then attempted to combine biomarkers to increase predictability using the following algorithm (FIG. 6*a*). Linear discriminant analysis was used to combine loci in a forward step-wise manner such that model included loci were those that increased the AUC of the discovery sample until the value was maximized. Ibis set of loci was then used to predict PPD status in the replication sample. The algorithm returned two loci at CpGs cg21326881 and cg00058938, corresponding to the promoter regions of the HP1BP3 and TTC9B genes, respectively, which resulted in an AUC of 0.92 in the discovery sample and 0.9 in the replication sample (FIG. 6*b*). A genome-wide significance for this biomarker set of p=0.041 was determined by Monte Carlo permutation analysis.

Figures 2A, 2B, 2C, 2D, 2E, 2F, 2G, 2H:
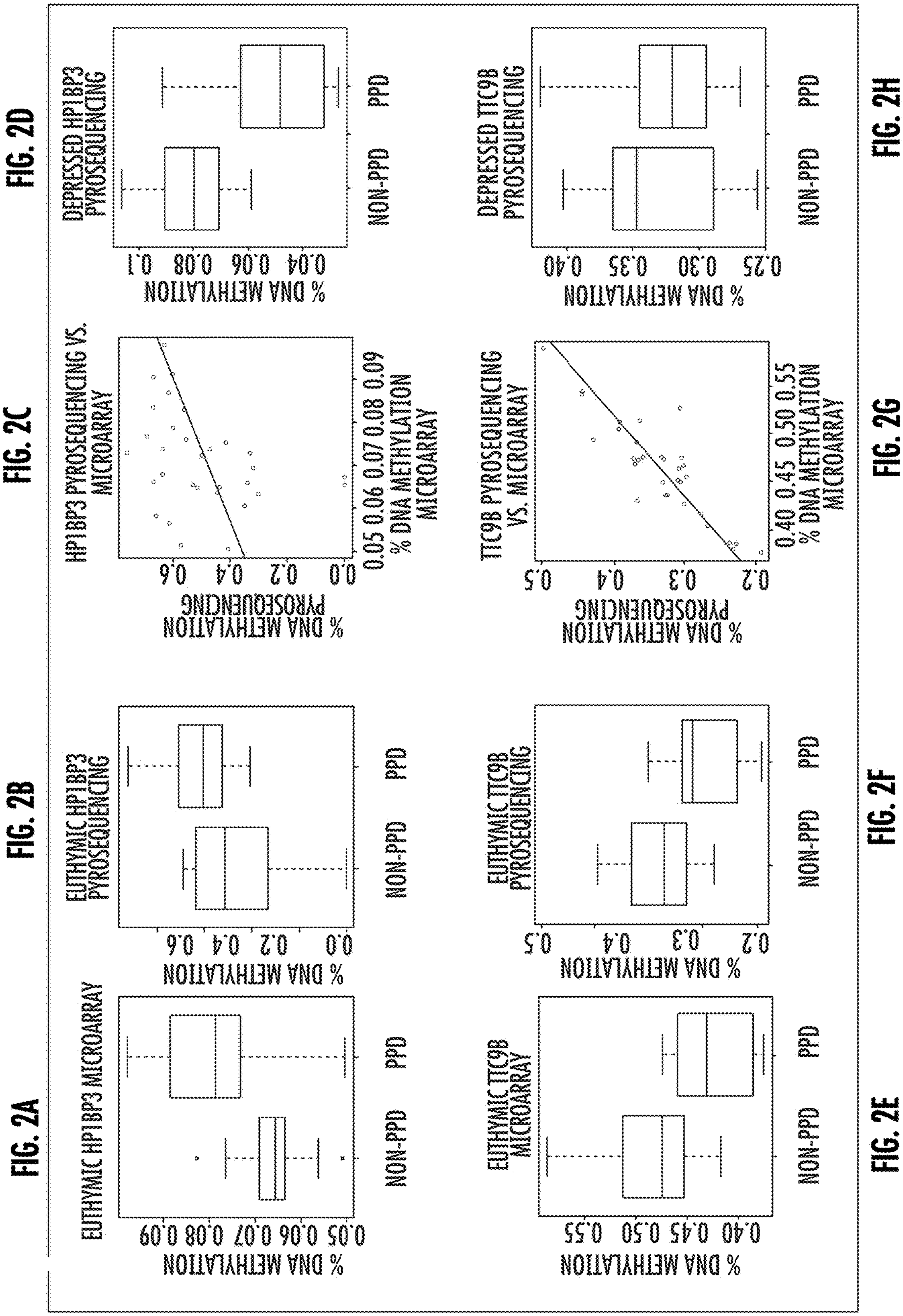
FIG. 2A-2H. Validation of biomarker loci. Boxplots of the percentage of DNA methylation in the non-PPD and PPD groups for HP1BP3 microarray (FIG. 2A) and pyrosequencing (FIG. 2B) and TTC9B microarray (FIG. 2E) and pyrosequencing (FIG. 2F) values. Scatter plots of the % DNA methylation difference between PPD minus non-PPD samples in the prepartum euthymic sample obtained by pyrosequencing (y-axis) and microarray (x-axis) is depicted for HP1BP3 (FIG. 2C) and TTC9B (FIG. 2G). Boxplots of the percentage of DNA methylation in the non-PPD and PPD groups for HP1BP3 pyrosequencing (FIG. 2D) and pyrosequencing (FIG. 2H) values obtained from the independent replication cohort of prepartum depressed women.

Example 4: Pyrosequencing Validation of Identified Biomarkers. We performed sodium bisulfite pyrosequencing to validate the microarray findings in the human sample at CpG dinucleotides located within the region chr1: 20986692-20986676 (strand −, human genome build hg18) and chr 19: 45416573 (strand +, human genome build hg18), located upstream of HP1BP3 and TTC9B, respectively. PPD status was significantly associated with the HP1BP3 microarray and pyrosequencing data and was significantly correlated between methods (FIG. 2ABC, Table 2). DNA methylation for TTC9B was significantly associated with PPD status for both the microarray and pyrosequencing data and was significantly correlated between the two methods (FIG. 2EFG, Table 2).

Using HP1BP3 and TTC9B pyrosequencing values in the prediction linear discriminant model, we obtained an AUC of 0.87 for the prepartum euthymic sample, which included three additional women not assessed via microarray (PPD N=13, non-PPD N=22). AUC values did not vary significantly when determined for blood collected in each trimester separately (AUC $1^{st}$=0.86, AUC $2^{nd}$=0.80, AUC $3^{rd}$=1). We next evaluated the performance of the biomarker loci on blood taken from the prepartum depressed sample. While the relative direction of TTC9B association with PPD status was similar to the prepartum euthymic women it was not significantly different (FIG. 2*h*, Table 2). For HP1BP3 the direction of association was significant but in the opposite direction to that observed in the prepartum euthymic cohort (FIG. 2*d*, Table 2). Linear discriminant model prediction of PPD status in this cohort returned an AUC of 0.12, which represents an 88% prediction accuracy of PPD status in the reverse direction.

TABLE 2

Descriptive statistics of biomarker loci

| | Method | PPD | non-PPD | P value |
|---|---|---|---|---|
| Prepartum Euthymic | | | | |
| HP1BP3 | Microarray | 0.08 ± 0.0012 | 0.067 ± 0.00034 | 0.0012 |
| | Pyrosequencing | 0.063 ± 0.0012 | 0.045 ± 0.00095 | 0.046 |
| | Method Correlation | | Spearman's Rho = 0.41 | 0.018 |
| TTC9B | Microarray | 0.42 ± 0.0036 | 0.48 ± 0.0021 | |
| | Pyrosequencing | 0.30 ± 0.0055 | 0.38 ± 0.0034 | 0.0046 |
| | Method Correlation | | Spearman's Rho = 0.81 | $2.6 \times 10^{-8}$ |
| Prepartum Depressed | | | | |
| HP1BP3 | Pyrosequencing | 0.05 ± 0.0017 | 0.081 ± 0.0024 | 0.0072 |
| TTC9B | Pyrosequencing | 0.32 ± 0.0035 | 0.33 ± 0.0079 | 0.84 |

Figures 3A, 3B, 3C, 3D:
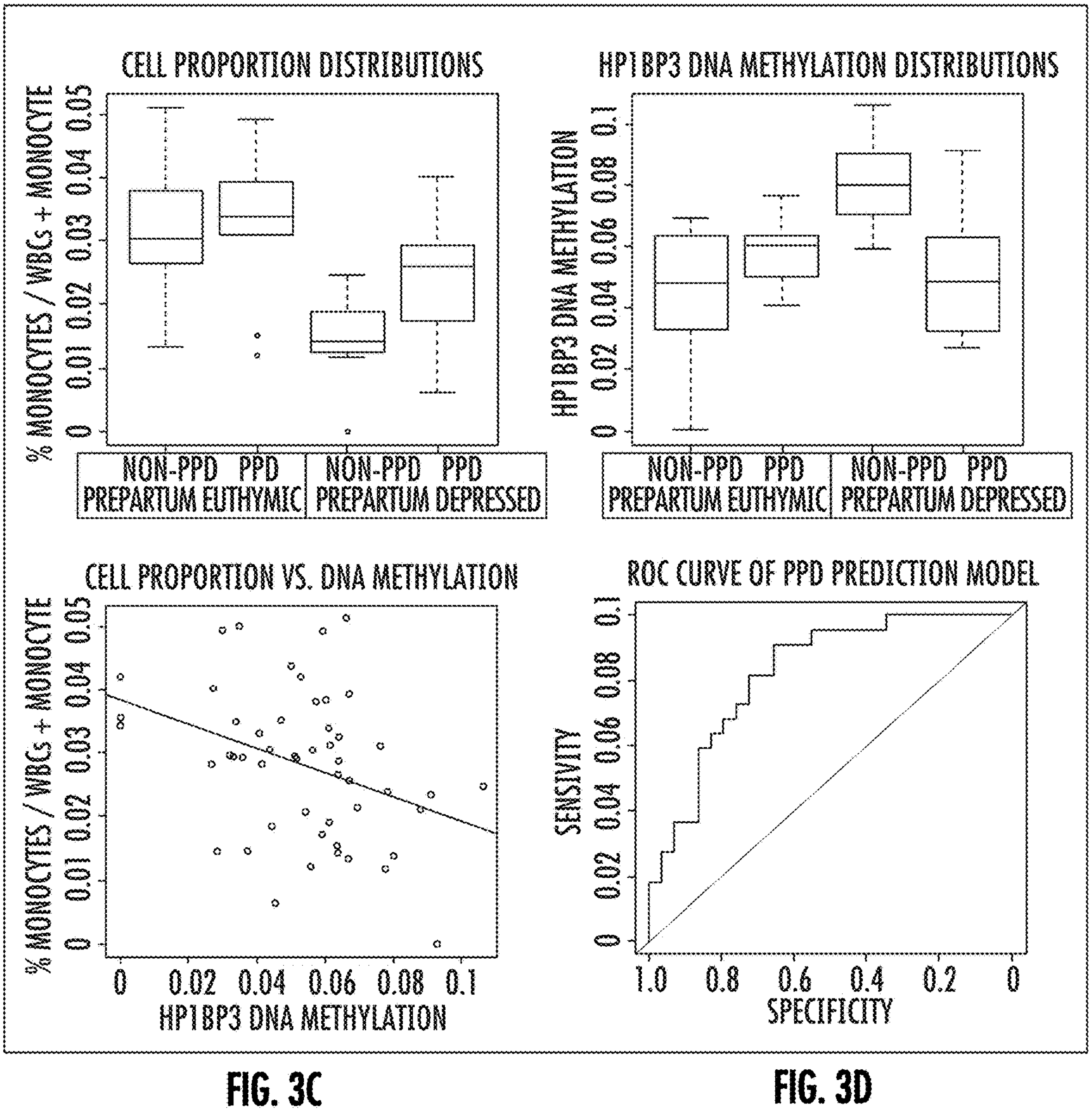
FIG. 3A-3D. Cell proportion and biomarker DNA methylation predict PPD.

Example 5: Biomarker Replication is Influenced by Blood Cellular Heterogeneity. We hypothesized that the discrepancy between the prepartum euthymic and depressed cohorts may be related to differences in blood cell-type counts between the two groups. Various experiments have identified elevated granulocytes and decreased CD8 and CD4 T cell and associated cytokine profiles in individuals exhibiting depressed mood[28, 29]. Using DNA methylation proxies in the 19 prepartum depressed and 32 prepartum euthymic women, we determined that cell-type proportions of CD8 T cells, CD4 T cells, B cells, and monocytes were significantly reduced in the depressed prepartum group, while cross batch controls exhibited non-significant differences in the opposite direction (Table 6). Pyrosequencing DNA methylation values for HP1BP3 were evaluated against all cell-types in an additive linear model and identified a trend with monocyte proportions (b=−1.11±0.6, p=0.07). We subsequently evaluated the ratio of monocytes to the summed proportions of CD8 T cells, CD4 T cells, B cells, and granulocytes and observed a significant association with prepartum depression status (cell ratio, Depressed=$0.021\pm5.2\times10^{-4}$, Euthymic=$0.032\pm3.3\times10^{-4}$, p=$2.1\times10^{-4}$) but not PPD status (cell ratio, PPD=$0.028\pm5\times10^{-4}$, non-PPD=$0.028\pm4.2\times10^{-4}$, p=0.86) (FIG. 3A), the distribution of which was similar but opposite to that of HP1BP3 DNA methylation (FIG. 3B). This monocyte to non-monocyte cell-type ratio was negatively correlated with DNA methylation of HP1BP3 (Spearman's Rho=−0.37, p=0.0074) (FIG. 3*c*), while TTC9B was not associated (Spearman's Rho=−0.22, p=0.11). Linear regression modeling was performed for PPD diagnosis against an interaction of HP1BP3 DNA methylation with the cell-type ratio, with TTC9B DNA methylation as a covariate. The model was significantly associated with PPD ($R^2$=0.38, p=$1.9\times10^{-4}$), as were all model terms including DNA methylation of HP1BP3 (β=−0.22±0.075, p=0.0044), TTC9B (β=−0.033±0.0081, p=$1.6\times10^{-4}$), the cell-type ratio (β=−49.66±14.64, p=0.0014), and the interaction between HP1BP3 DNA methylation and cell-type ratio (β=8.03±2.4, p=0.0016). Using a bootstrapping method, we predicted PPD status for each individual using the linear model and obtained an AUC of 0.82 (FIG. 3D).

Importantly, the cell proxy analysis only takes into account the relative percentage of various cell-types, but not the overall white blood cell (WBC) count. Where available, prepartum WBC counts and proportions of lymphocytes, granulocytes, and monocytes were obtained from complete blood count (CBC) data (N=17 women). CBC derived total WBC counts were negatively correlated with the proxy derived monocyte to non-monocyte ratio (Spearman's Rho=−0.7, p=0.02), suggesting the decreased cell-type ratio observed in the prepartum depressed group may be indicative of elevated WBC counts and depression associated inflammation. This effect appeared to be driven by a positive correlation of WBC count with granulocyte proportion (Spearman's Rho=0.92, p=$2.2\times10^{-16}$), which is consistent with the above cited elevations in granulocyte levels with depression[28]. The ratio of CBC derived monocyte to non-monocyte (lymphocytes and granulocytes) ratio did not correlate with those derived by DNA methylation proxy (Spearman's Rho=0.24, p=0.36). We limited the analysis to only those 11 samples where CBC data was derived from within the same trimester as the blood draw used for microarray analysis and observed a significant correlation (Spearman's Rho=0.66, p=0.044). We attempted to predict PPD status via bootstrap analysis across all 17 individuals using the linear model generated above with CBC data based monocyte to non-monocyte ratios in place of proxy based ratios and generated a highly accurate prediction of PPD status (AUC=0.96) (FIG. 3*d*).

Figure 7B:
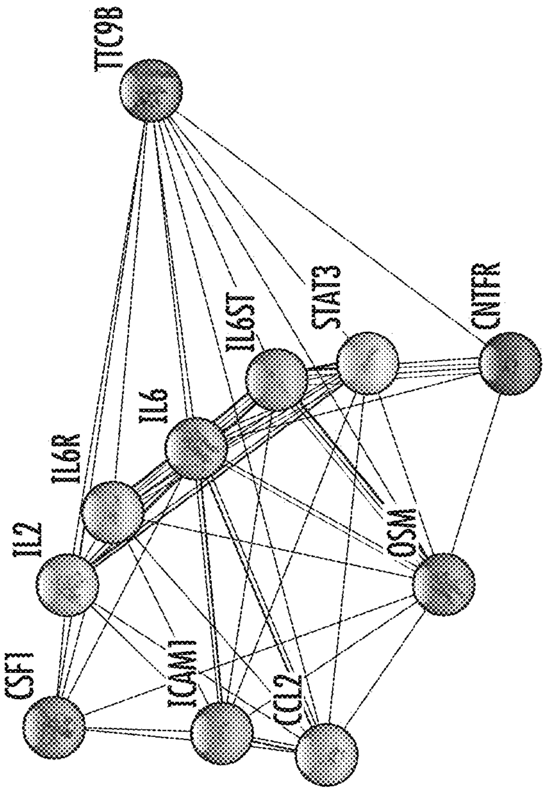
FIG. 7A-7B. STRING implicated gene interactions. Gene interactions implicated by the STRING database for HP1BP3 (FIG. 7A) and TTC9B (FIG. 7B). Green, blue, red, and black lines represent connections based on text mining algorithms, interaction databases, experimental evidence, and co-expression experiments, respectively.
Figure 7A:
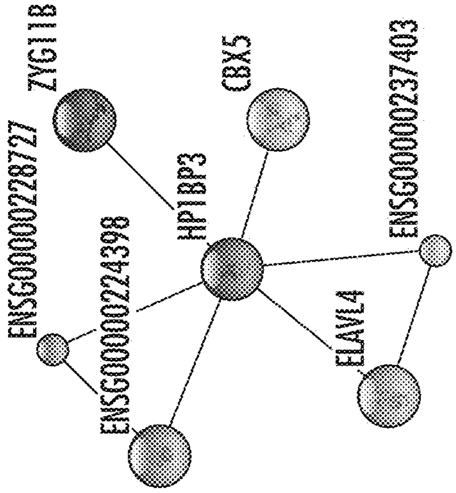
Figures 8A, 8B, 8C, 8D:
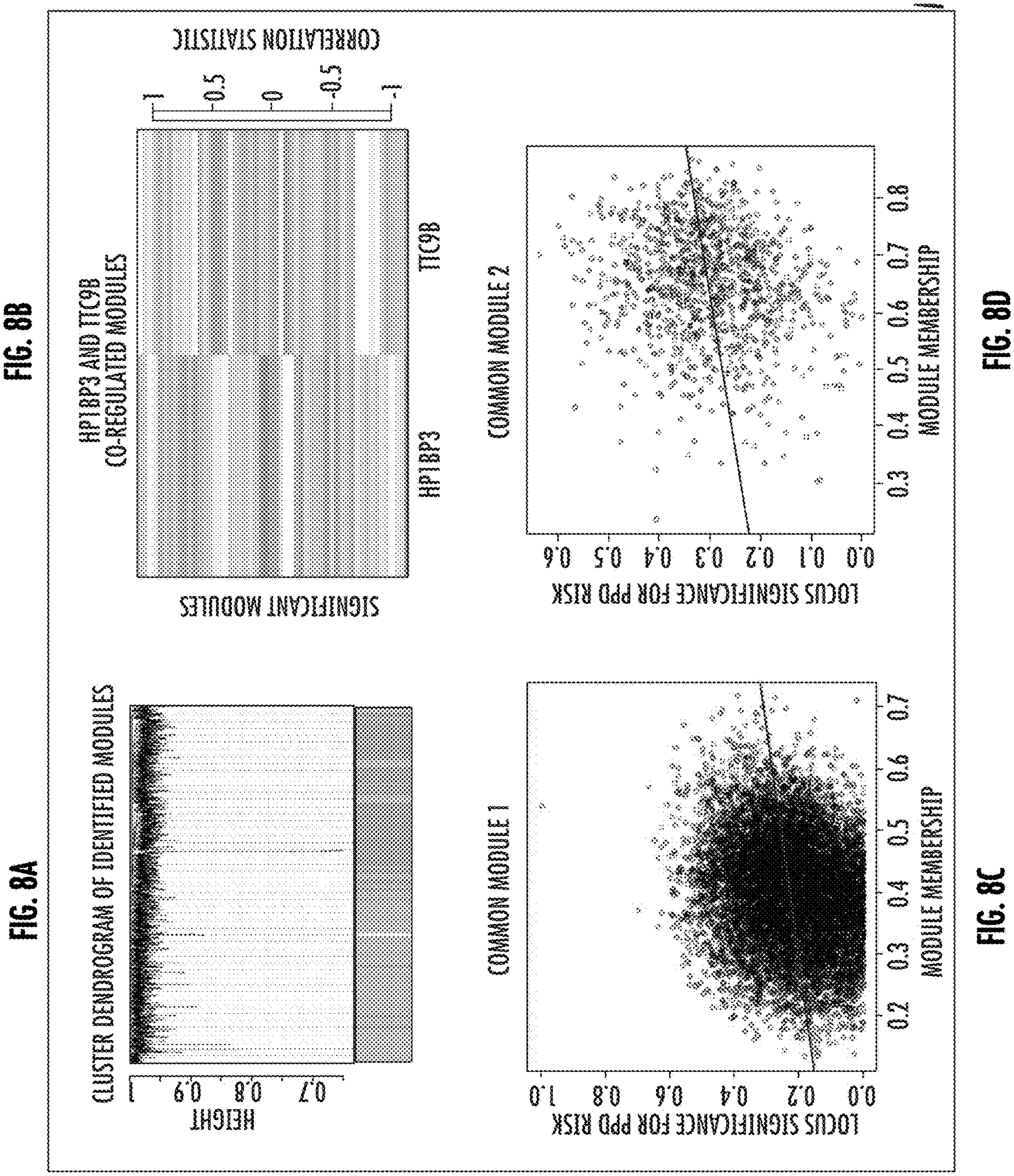
FIG. 8A-8D. HP1BP3 and TTC9B co-regulated networks.

Example 6: Functional Classification of HP1HP3 and TTC9B. We attempted to ascertain the function of HP1BP3 and TTC9B loci bioinformatically by using the STRING database[30] (FIG. 7) and by performing weighted gene co-expression network analysis (WGCNA)[16] against DNA methylation of the HP1BP3 CpG (cg21326881) and TTC9B CpG (cg00058938) as the target variables for correlation (FIG. 8). The resulting networks of HP1BP3 and TTC9B co-regulated genes were strikingly anti-correlated (Spearman's Rho=−0.76, $p=2.2\times10^{-16}$), suggesting HP1BP3 and TTC9B are co-regulated (FIG. 8*b*). Resultantly, we limited networks to those demonstrating significant non-parametric correlation between module membership and correlation significance per group and identified two co-regulated networks significantly associated across both genes (Module 1: HP1BP3 Rho=0.56, $p=8.8\times10^{-4}$, TTC9B Rho=−0.54, p=0.0015, Module 2: HP1BP Rho=0.45, p=0.0087, TTC9B Rho=−0.46, p=0.0081) (FIG. 8CD). No significantly enriched pathways were identified by g. Profiler in module 2; however, module 1 contained a number of significantly enriched KEGG pathways that can be tied to the antidepressant functions of E2 in the hippocampus (Table 7, not shown).

Figures 9A, 9B, 9C:
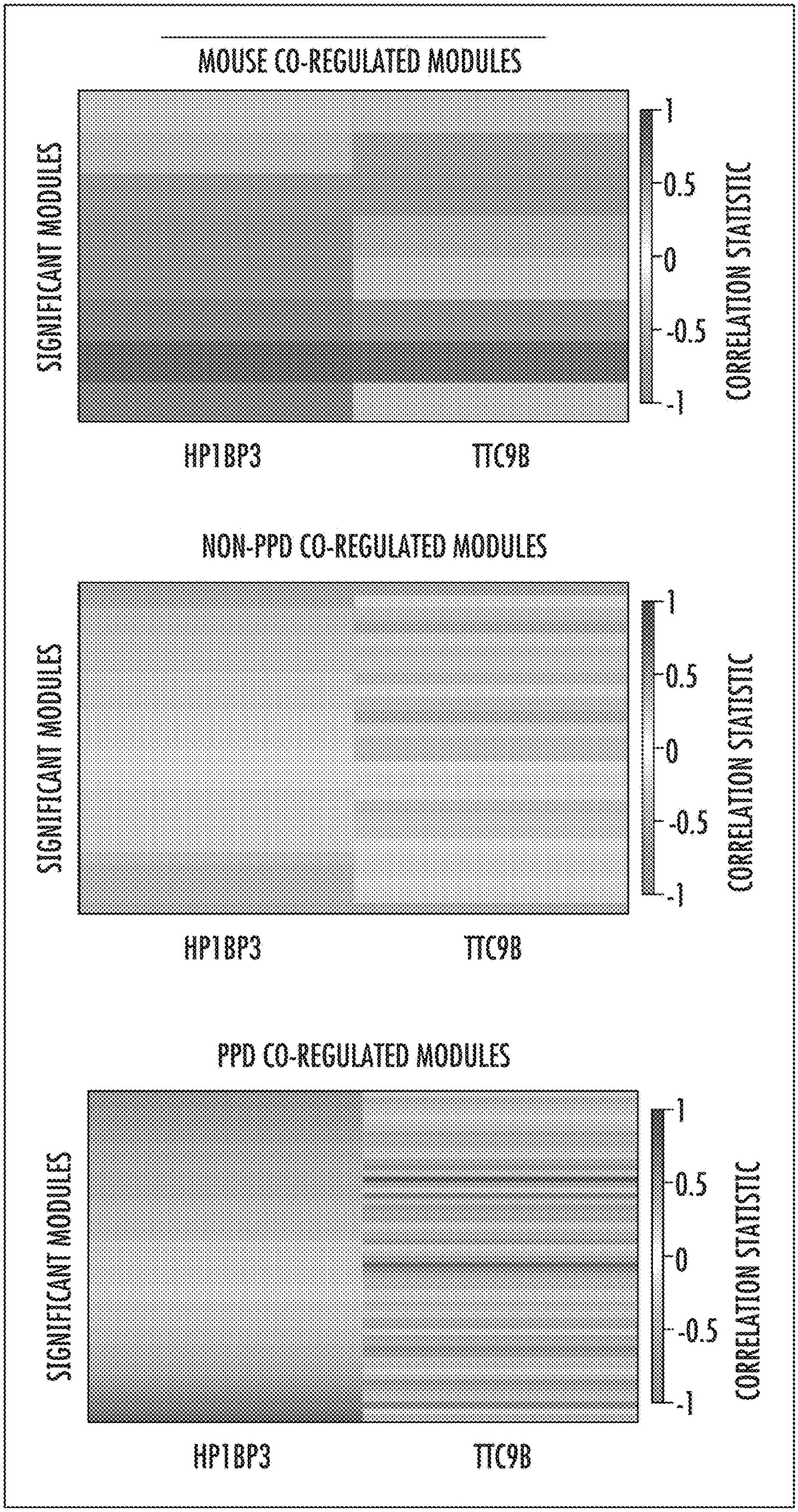
FIG. 9A-9C. HP1BP3 and TTC9B co-regulated networks by phenotype.

We applied WGCNA within the PPD and non-PPD women separately, as well as within the mouse E2 DMR data to ascertain the normal co-regulation pattern of HP1BP3 and TTC9B genes. The pattern of gene co-regulation was positively correlated between HP1BP3 and TTC9B in non-PPD cases and mice, but anti-correlated in PPD cases (FIG. 9), and is consistent with the proposed heightened sensitivity to E2 mediated epigenetic reprogramming in the PPD group.

Figure 10:
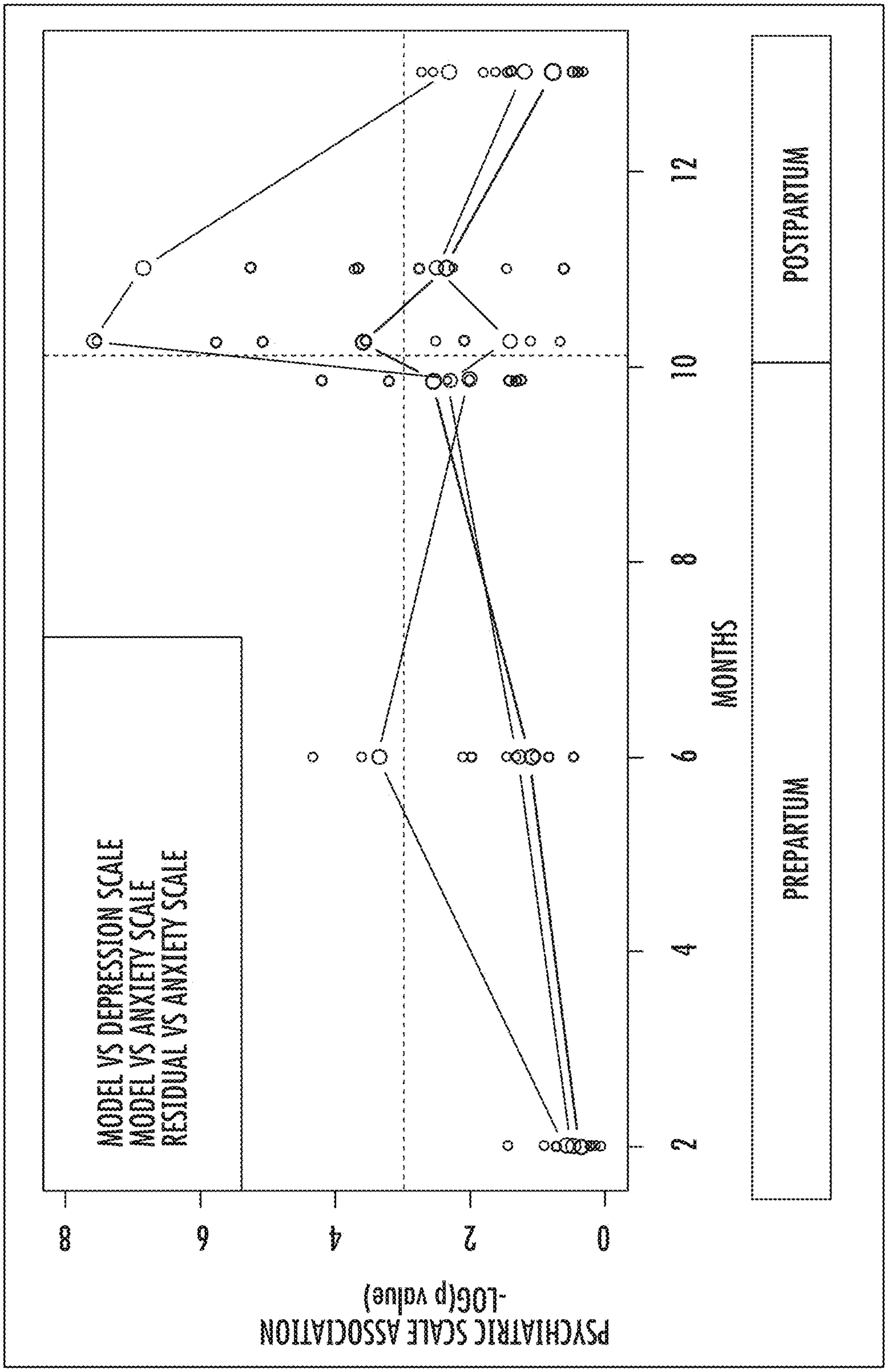
FIG. 10. A plot depicting the −log (p value) of the association PPD predictive model components with depressive scales (EPDS, MADRS, IDS-SR) (black) and anxiety and sleep scales (PSS, CGIS, PSQI) (blue) as a function of time points during pregnancy and postpartum (x axis). PPD predictive model residuals are also plotted against anxiety and sleep scales (PSS, CGIS, PSQI) (red) for each longitudinal time point in the human study. Mean values for each scale grouping are depicted with a solid line and larger dot. Values over the horizontal green line represent significant associations. The vertical black line represents parturition.

Example 6: Association of Phenotype Information with the PPD Prediction Model. In order to expand upon the main findings of our published research, we took advantage of extensive phenotype information collected longitudinally. While our biomarker algorithm was capable of predicting PPD with 82% accuracy, we first asked if we would observe associations between the PPD predictive model and continuous depression scale ratings taken from the Edinburgh Postnatal Depression Screen (EPDS), the Montgomery Asperg Depression Rating Scale (MADRS), and the Index of Depressive Symptomology—Self Report (IDS-SR). Significant associations with the PPD predictive model were observed at the 1 week (1W) and 1 month (1M) time points following parturition (FIG. 10). We next asked if additionally collected phenotype information could explain the remaining variance by investigating associations of collected variables with the PPD prediction model residuals, or in other words, with what was NOT accounted for by our model. We identified significant associations between these PPD model residuals and number of metrics associated with stress and anxiety as well as sleep quality occurring in the 1W and 1M time points. These included metrics from the Perceived Stress Scale (PSS) (1W:Rho=0.4, p=0.024; 1M: Rho=0.42, p=0.006), the Clinical Global Impression Scale (CGIS) (1W:Rho=0.4, p=0.009; 1M: Rho=0.63, $p=4.7\times10^{-6}$), and the Pittsburgh Sleep Quality Index (PSQI) scale (1W:Rho=0.61, $p=2.3\times10^{-4}$; 1M: Rho=0.31, p=0.046) (FIG. 10). By contrast, the standard PPD model did not account for this PPD associated variance (FIG. 10). Together, these results suggest that PPD predictive biomarkers TTC9B and HP1BP3 may account for more depressive as opposed to anxious aspects of PPD. To test the assertion that controlling for anxiety or sleep metrics was not accounted for by PPD model prediction, we re-assessed PPD model prediction accuracy using these metrics taken at the time of blood draw for our combined cohort of antenatally euthymic as well as antenatally depressed women. Using metrics from the CGIS, PSS, and PSQI as an additive covariate in our model, we improved our AUC from 0.82 to 0.85, 0.85, and 0.88, respectively.

We next reasoned that as we were able to find DNA methylation proxies for depressive phenotype, we may be able to find additional biomarker candidates for this proposal capable of acting as a biomarker of the unaccounted for sleep/anxiety component. We found that anxiety and sleep components were generally highly correlated across the antenatal to postpartum periods (For example: CGIS 3$^{rd}$ trimester vs. CGIS 1M: Rho=0.54, $3.7\times10^{-5}$, and: PSS 3$^{rd}$ trimester vs. PSS 1M: Rho=0.62, $3.5\times10^{-5}$). This accounts for the fact that stress metrics measured at the time of blood draw added to PPD predictive accuracy as measured by AUC above and supports the idea that epigenetic factors correlating with stress and sleep metrics at the time of blood draw may be used as proxies to improve our model accuracy.

To search for these additional candidate biomarkers, we correlated PSS, CGIS, and PSQI scores obtained at the time of blood draw with DNA methylation at each microarray position in a non-parametric manner. Similarly, we identified those loci significantly correlated with PPD model residuals, recognizing that additional dimensions of the original PPD diagnosis may be accounted for by measures not accounted for by the anxiety and sleep metrics. This screen resulted in 463 loci significantly associated across all factors at the 5% level. Gene Ontology analysis revealed a significant enrichment for genes associated with 'neuron projection development' (GO:0031175, p=0.0074) in this group, which is consistent with the proposed role of TTC9B and HP1BP3 DNA methylation variation as well as the known antidepressant functions of estrogen in the hippocampus. We then used only the 26 genes within this category and attempted PPD diagnosis prediction with DNA methylation variation at these genes in place of PSS, CGIS, or PSQI scale metrics and obtained AUC values ranging from 0.79 to 0.9. By taking the top 99$^{th}$ percentile of these AUC measurements, we generated the list of additional experimentally implicated biomarkers in Table 2. Similarly, we assessed the added predictive capacity of stress related genes where gene expression variation was previously associated with antenatal depression and obtained improved model prediction in some cases (Table 6).

TABLE 6

Candidate loci for epigenetic analysis

| Illumina ID | Gene | Model Prediction Improvement | Functional Summary | Pubmed ID |
|---|---|---|---|---|
| Literature Implicated | | | | |
| cg00058938 | TTC9B | NA | PPD epigenetic biomarker | PMID: 23689534 |
| cg21326881 | HP1BP3 | NA | PPD epigenetic biomarker | PMID: 23689534 |
| cg12695586 | OXTR | NA | PPD epigenetic biomarker, inflammation proxy | PMID: 16787287 |

TABLE 6-continued

| Candidate loci for epigenetic analysis | | | | |
|---|---|---|---|---|
| Illumina ID | Gene | Model Prediction Improvement | Functional Summary | Pubmed ID |
| cg15910486 | NR3C1 | 0.89 | Glucocorticoid receptor gene | PMID: 21995950 |
| cg19014730 | FKBP5 | 0.88 | Glucocorticoid receptor modulator | PMID: 21995950 |
| cg21614231 | BAG1 | 0.86 | Glucocorticoid receptor chaparone | PMID: 21995950 |
| cg21146273 | GLUR1 | 0.78 | AMPA receptor subunit gene | PMID: 21159965 |
| cg25148589 | GLUR2 | 0.82 | AMPA receptor subunit gene | PMID: 21159965 |
| Experimentally Implicated | | | | |
| cg22129545 | CLMN | 0.90 | Hippocampal neuron specific: actin cytoskeleton: LTP | PMID: 20014094 |
| cg23660155 | MBP | 0.89 | Inflammation, estrogen, and synaptic transmission | PMID: 20060814 |
| cg27380774 | AP2A2 | 0.89 | Mediation of AMPA receptor trafficking | PMID: 17289840 |
| cg09034795 | COL9A3 | 0.89 | Sex determination | PMID: 23874228 |
| cg03202693 | CAMK2B | 0.88 | Stress associated neuroplasticity, suicidality | PMID: 21847376 |
| cg12737854 | GDPD5 | 0.88 | Neurite formation, neurogenesis | PMID: 23329048 |
| cg09480289 | PLXNA1 | 0.88 | Axon Guidance | PMID: 22998873 |
| cg06960600 | UCHL1 | 0.88 | Neuroprotection | PMID: 23900885 |
| cg12985204 | AGAP2 | 0.87 | Mediation of AMPA receptor trafficking | PMID: 21847098 |
| cg23098038 | KIF13B | 0.87 | Hippocampal dendritic vesical modulation | PMID: 22908316 |
| cg08694295 | DSCAML1 | 0.87 | Axon Guidance | PMID: 20882566 |
| cg07804196 | MAPK8IP3 | 0.87 | Axon Elongation | PMID: 23576431 |
| cg14795572 | NRTN | 0.87 | Neuroprotection | PMID: 15919076 |
| cg03257547 | CACNA1C | 0.86 | Major Depression, hippocampal function | PMID: 23860750 |

To summarize, we identified two epigenetic biomarkers predictive of postpartum depression independent of antenatal depression status with an accuracy of 82%. A search for additional factors capable of improving prediction accuracy demonstrated that incorporation of additional anxiety and sleep metrics improved model accuracy to ~88%. Epigenetic proxies correlated with these factors had similar prediction enhancing effects (Table 2). Sleep quality had the strongest prediction enhancing effect. Interestingly, a recent randomized clinical trial of two sleep medications administered during the third trimester were shown to significantly reduced depression symptoms at 2 and 6 weeks postpartum. However, as sleep quality is often comorbid with anxiety and anxiety metrics also improved model prediction, it is difficult to separate one from the other. Additionally, sleep has been demonstrated to be important for hippocampal based memory consolidation, which relies in part on AMPA receptor function. In our previous work the TTC9B PPD biomarker was hypothesized to modulate AMPA receptor levels, which in turn have been demonstrated to be critical for resilience or vulnerability to stress. It has been posited by many that risk to PPD may be related to an increased vulnerability to stressors in the postpartum period. Together, the data suggest that our previously identified biomarkers may be related to sleep and stress related vulnerability systems, but that the biological variation encoded in TTC9B DNA methylation is insufficient to completely influence the sleep and anxiety phenotypes related to PPD and thus to capture the full extent of PPD risk variation. Incorporation of additional metrics and epigenetic proxies of those metrics allow for additional model prediction accuracy.

Example 7: Oxytocin Receptor Biomarker. We interrogated DNA methylation variation in the oxytocin receptor (OXTR) gene promoter using pyrosequencing in a region implicated by our microarray data as potentially associated with PPD. A recent randomized clinical trial of postpartum mood and oxytocin administration provided suggestive evidence of a moderating effect of childhood trauma on oxytocin related mood. In our study, we identified a significant interaction between early childhood sexual abuse and oxytocin receptor DNA methylation on PPD diagnosis (3=−0.38±0.18, p=0.036). Importantly, we also noticed a significant association of OXTR DNA methylation with antenatal depression status (=−0.16±0.08, p=0.05). As oxytocin is heavily implicated in modulating inflammation and we previously identified a significantly lower ratio of monocytes to non-monocytes with antenatal depression, we hypothesized that epigenetic variation at the OXTR may be driving inflammatory cell type differences observed. In fact, OXTR methylation was significantly associated with the monocytes to non-monocyte cell type ratio (Rho=0.33, p=0.021). Thus, in some embodiments, OXTR DNA methylation information can be used in addition to the other biomarkers or alternatively, it can be imported into our predictive model in place of monocyte to non-monocyte ratio. Using OXTR in the model to predict just the antenatally euthymic women performs identically to using cell type ratio with an AUC of 0.90. Incorporation of antenatally depressed women for a complete sample of N=51 women generates an AUC of 0.74, while incorporation of PSQI scores improved the AUC to 0.82. While the model was not improved, it suggests that OXTR epigenetic variation emulates the important aspects of inflammatory cell type variation to some degree and may be used when it is not possible to obtain information on the cell type proportions.

Discussion

We addressed the hypothesis that regions of E2 mediated epigenetic change may predict PPD risk. Numerous correlations linking E2 mediated epigenetic change with DNA methylation changes occurring in the PPD risk population were identified in both the original prepartum euthymic cohort as well as in the independent replication cohort of women depressed during pregnancy. Cumulatively, the results suggest a systematic increase in DNA methylation change occurs in the blood of the PPD group during a period where pregnancy hormones are at high levels. As gonadal hormone levels have been shown not to predict PPD risk, these data provide suggestive evidence that the underlying risk in this group may be related to an increased sensitivity for epigenetic change in response to normal levels of circulating hormones. It is important to consider that the sample sizes interrogated in the mouse experiments were small, and that higher powered experiments may identify additional genomic regions of E2 responsive DNA methylation change in the hippocampus. The findings of enriched SP-1 binding sites and increased evidence for hippocampal LTP associated genes in E2 responsive DMRs is consistent with the known downstream transcription factor activation[31-34] as well as antidepressant functions of E2 exposure in the hippocampus[35] and adds confidence to the assertion that we are detecting true E2 DMRs.

CpG methylation levels at two loci within the HP1BP3 and TTC9B genes were identified as biomarkers predictive of PPD. Both genes have ties to estrogen signaling, as HP1BP3 was identified to associate with ER β based on tandem affinity purification assays performed on MCF-7 breast cancer cells[36] and TTC9B expression has been shown to be responsive to gonadal hormones[37]. Due to the circulating nature of estrogen, the identification of these markers in peripheral blood may be a marker of estrogen mediated epigenetic changes occurring in the hippocampus and potentially conferring risk to phenotype based on its actions in the brain. The functional relevance of TTC9B may be linked to hippocampal synaptic plasticity as tetratricopeptide repeat containing domains such as that found in TTC9B have been shown to inhibit HSP90 mediated trafficking of AMPA receptors critical for hippocampal LTP/LTD[38].

While there have been numerous attempts to generate biomarkers for PPD[39-44], few studies report a high prediction accuracy. To our knowledge, the identified biomarkers represent the first prospective epigenetic biomarkers capable of predicting PPD status with over 80% accuracy from blood. Segregation of the sample by the trimester of blood collection did not appear to affect prediction accuracy. These results suggest that epigenetic variation at biomarker loci is established early on during pregnancy and may represent a latent epigenetic status in the PPD risk group independent of pregnancy. The clinical implications of this finding are that early screening of those at risk for PPD may be possible, allowing an earlier direction of clinical treatment course.

The high prediction accuracy of the identified biomarkers was replicated in an independent cohort of women who were depressed during pregnancy. In this group, the PPD status was segregated with 88% accuracy; however, the prediction was in the opposite direction, driven by differences at the HP1BP3 locus. An analysis of cell-subfraction distributions across cohorts identified a difference in the ratio of monocytes to lymphocytes and granulocytes significantly decreased in the depressed cohort that appeared to account for the discrepancy. Our data is consistent with genome-wide expression studies of WBCs taken from women after parturition that demonstrated an association of immune system related genes with depression scores[44]. Incorporation of the DNA methylation biomarkers with cell count data enabled the prediction of PPD status in the entire cohort of 51 women with an AUC of 0.82. A potential confounding factor is that DNA methylation between the prepartum euthymic and depressed cohorts was assessed in two separate batches, as all initial analyses were performed on the euthymic cohort only. To control for this, we normalized DNA methylation levels at all 473 loci used for blood count proxy analysis using a cross batch control. The predicted cell-type proportions at these controls showed moderate but non-significant batch effects between cohorts (Table 5); however, the effects were in the opposite direction to the prepartum mood status association observed, suggesting this association is a true effect of prepartum mood status. Additionally, the significant correlation observed with CBC derived values adds confidence to assertion that the proxy derived values are representative of actual cell sub-type proportions. Finally, the linear model incorporating CBC derived cell proportions generated a highly accurate prediction of PPD status (AUC=0.96). Due to the small size the subsample used for this prediction, larger prospective cohorts will be required to validate the predictive efficacy of this model. Cumulatively, our data suggest that cell count information in combination with DNA methylation at HP1BP3 and TTC9B, successfully and accurately predicts PPD status independent of prepartum mood status.

The results of this study suggest that an increased sensitivity to E2 based epigenetic reprogramming may represent a molecular mechanism of predisposition to PPD risk. Future studies will be needed to rigorously test this hypothesis and track epigenetic changes through the course of pregnancy in women at risk and not at risk for PPD. The investigated population was in women with a previous history of mood disorders; however, studies investigating the efficacy PPD prediction in the general population will need to be determined. Accurate prediction of PPD status will enhance the clinical management of psychiatric treatment during the course of pregnancy.

REFERENCES

1. O'Hara M W. Postpartum depression: what we know. *J Clin Psychol* 2009; 65(12): 1258-1269.
2. Soufia M, Aoun J, Gorsane M A, Krebs M O. SSRIs and pregnancy: a review of the literature. Encephale 2010; 36(6): 513-516.
3. Field T. Prenatal depression effects on early development: a review. Infant Behav Dev 2011; 34(1): 1-14.
4. Breese McCoy S J. Postpartum depression: an essential overview for the practitioner. South Med J 2011; 104(2): 128-132.
5. Cuijpers P, Brannmark J G, van Straten A. Psychological treatment of postpartum depression: a meta-analysis. *J Clin Psychol* 2008; 64(1): 103-118.
6. Hirst K P, Moutier C Y. Postpartum major depression. *Am Fam Physician* 2010; 82(8): 926-933.
7. Marcus S M. Depression during pregnancy: rates, risks and consequences—Motherisk Update 2008. *Can J Clin Pharmacol* 2009; 16(1): e15-22.
8. Pinette M G, Wax J R. The management of depression during pregnancy: a report from the American Psychiatric Association and the American College of Obstetricians and Gynecologists. *Obstet Gynecol* 2010; 115(1): 188-189; author reply 189.
9. Studd J W. A guide to the treatment of depression in women by estrogens. *Climacteric* 2011.
10. Bloch M, Schmidt P J, Danaceau M, Murphy J, Nieman L, Rubinow D R. Effects of gonadal steroids in women with a history of postpartum depression. *Am J Psychiatry* 2000; 157(6): 924-930.
11. Bloch M, Rubinow D R, Schmidt P J, Lotsikas A, Chrousos G P, Cizza G. Cortisol response to ovine corticotropin-releasing hormone in a model of pregnancy and parturition in euthymic women with and without a history of postpartum depression. *J Clin Endocrinol Metab* 2005; 90(2): 695-699.

12. Kangaspeska S, Stride B, Metivier R, Polycarpou-Schwarz M, Ibberson D, Carmouche R P et al. Transient cyclical methylation of promoter DNA. *Nature* 2008; 452(7183): 112-115.
13. Kaminsky Z A, Tang T, Wang S C, Ptak C, Oh G H, Wong A H et al. DNA methylation profiles in monozygotic and dizygotic twins. *Nat Genet* 2009; 41(2): 240-245.
14. Schumacher A, Kapranov P, Kaminsky Z, Flanagan J, Assadzadeh A, Yau P et al. Microarray-based DNA methylation profiling: technology and applications. *Nucleic Acids Res* 2006; 34(2): 528-542.
15. Houseman E A, Accomando W P, Koestler D C, Christensen B C, Marsit C J, Nelson H H et al. DNA methylation arrays as surrogate measures of cell mixture distribution. *BMC Bioinformatics* 2012; 13(1): 86.
16. Langfelder P, Horvath S. WGCNA: an R package for weighted correlation network analysis. *BMC Bioinformatics* 2008; 9: 559.
17. Walf A A, Koonce C J, Frye C A. Estradiol or diarylpropionitrile decrease anxiety-like behavior of wildtype, but not estrogen receptor beta knockout, mice. *Behav Neurosci* 2008; 122(5): 974-981.
18. Osterlund M K, Witt M R, Gustafsson J A. Estrogen action in mood and neurodegenerative disorders: estrogenic compounds with selective properties—the next generation of therapeutics. *Endocrine* 2005; 28(3): 235-242.
19. Lund T D, Rovis T, Chung W C, Handa R J. Novel actions of estrogen receptor-beta on anxiety-related behaviors. *Endocrinology* 2005; 146(2): 797-807.
20. Walf A A, Rhodes M E, Frye C A. Antidepressant effects of ERbeta-selective estrogen receptor modulators in the forced swim test *Pharmacol Biochem Behav* 2004; 78(3): 523-529.
21. Walf A A, Frye C A. ERbeta-selective estrogen receptor modulators produce antianxiety behavior when administered systemically to ovariectomized rats. *Neuropsychopharmacology* 2005; 30(9): 1598-1609.
22. MacLusky N J, Luine V N, Hajszan T, Leranth C. The 17alpha and 17beta isomers of estradiol both induce rapid spine synapse formation in the CA1 hippocampal subfield of ovariectomized female rats. *Endocrinology* 2005; 146 (1): 287-293.
23. ter Horst G J. Estrogen in the limbic system. *Vitam Horm* 2010; 82: 319-338.
24. Suda S, Segi-Nishida E, Newton S S, Duman R S. A postpartum model in rat: behavioral and gene expression changes induced by ovarian steroid deprivation. *Biol Psychiatry* 2008; 64(4): 311-319.
25. Green A D, Galea L A. Adult hippocampal cell proliferation is suppressed with estrogen withdrawal after a hormone-simulated pregnancy. *Horm Behav* 2008; 54(1): 203-211.
26. Beissbarth T, Speed T P. GOstat: find statistically overrepresented Gene Ontologies within a group of genes. *Bioinformatics* 2004; 20(9): 1464-1465.
27. Reimand J, Kull M, Peterson H, Hansen J, Vilo J. g:Profiler—a web-based toolset for functional profiling of gene lists from large-scale experiments. *Nucleic Acids Res* 2007; 35 (Web Server issue): W193-200.
28. Shimamiya T, Terada N, Wakabayashi S, Mohri M. Mood change and immune status of human subjects in a 10-day confinement study. *Aviat Space Environ Med* 2005; 76(5): 481-485.
29. Lutgendorf S K, Lamkin D M, DeGeest K, Anderson B, Dao M, McGinn S et al. Depressed and anxious mood and T-cell cytokine expressing populations in ovarian cancer patients. *Brain Behav Immun* 2008; 22(6): 890-900.
30. Snel B, Lehmann G, Bork P, Huynen M A. STRING: a web-server to retrieve and display the repeatedly occurring neighbourhood of a gene. *Nucleic Acids Res* 2000; 28(18): 3442-3444.
31. Guido C, Panza S, Santoro M, Avena P, Panno M L, Perrotta I et al. Estrogen receptor beta (ERbeta) produces autophagy and necroptosis in human seminoma cell line through the binding of the Sp1 on the phosphatase and tensin homolog deleted from chromosome 10 (PTEN) promoter gene. *Cell Cycle* 2012; 11(15): 2911-2921.
32. Bartella V, Rizza P, Barone I, Zito D, Giordano F, Giordano C et al. Estrogen receptor beta binds Sp1 and recruits a corepressor complex to the estrogen receptor alpha gene promoter. *Breast Cancer Res Treat* 2012; 134(2): 569-581.
33. Ruegg J, Cai W, Karimi M, Kiss N B, Swedenborg E, Larsson C et al. Epigenetic regulation of glucose transporter 4 by estrogen receptor beta. *Mol Endocrinol* 2011; 25(12): 2017-2028.
34. Vivar O I, Zhao X, Saunier E F, Griffin C, Mayba O S, Tagliaferri M et al. Estrogen receptor beta binds to and regulates three distinct classes of target genes. *J Biol Chem* 2010; 285(29): 22059-22066.
35. Ramanan V K, Kim S, Holohan K, Shen L, Nho K, Risacher S L et al. Genome-wide pathway analysis of memory impairment in the Alzheimer's Disease Neuroimaging Initiative (ADNI) cohort implicates gene candidates, canonical pathways, and networks. *Brain Imaging Behav* 2012.
36. Nassa G, Tarallo R, Ambrosino C, Bamundo A, Ferraro L, Paris O et al. A large set of estrogen receptor beta-interacting proteins identified by tandem affinity purification in hormone-responsive human breast cancer cell nuclei. *Proteomics* 2011; 11(1): 159-165.
37. Cao S, Iyer J K, Lin V. Identification of tetratricopeptide repeat domain 9, a hormonally regulated protein. *Biochem Biophys Res Commun* 2006; 345(1): 310-317.
38. Gerges N Z, Tran I C, Backos D S, Harrell J M, Chinkers M, Pratt W B et al. Independent functions of hsp90 in neurotransmitter release and in the continuous synaptic cycling of AMPA receptors. *J Neurosci* 2004; 24(20): 4758-4766.
39. Kuijpens J L, Vader H L, Drexhage H A, Wiersinga W M, van Son M J, Pop V J. Thyroid peroxidase antibodies during gestation are a marker for subsequent depression postpartum. *Eur J Endocrinol* 2001; 145(5): 579-584.
40. Skrundz M, Bolten M, Nast I, Hellhammer D H, Meinlschmidt G. Plasma oxytocin concentration during pregnancy is associated with development of postpartum depression. *Neuropsychopharmacology* 2011; 36(9): 1886-1893.
41. Yim I S, Glynn L M, Schetter C D, Hobel C J, Chicz-Demet A, Sandman C A. Prenatal beta-endorphin as an early predictor of postpartum depressive symptoms in euthymic women. *J Affect Disord* 2010; 125(1-3): 128-133.
42. Licinio J. Potential diagnostic markers for postpartum depression point out to altered immune signaling. *Mol Psychiatry* 2010; 15(1): 1.
43. Albacar G, Sans T, Martin-Santos R, Garcia-Esteve L, Guillamat R, Sanjuan J et al. Thyroid function 48 h after delivery as a marker for subsequent postpartum depression. *Psychoneuroendocrinology* 2010; 35(5): 738-742.
44. Segman R H, Goltser-Dubner T, Weiner I, Canetti L, Galili-Weisstub E, Milwidsky A et al. Blood mononuclear cell gene expression signature of postpartum depression. *Mol Psychiatry* 2010; 15(1): 93-100, 102.

We claim:

1. A method for treating post-partum depression (PPD) in a patient having or at risk of having PPD, comprising:

a) analyzing DNA methylation levels of a panel of biomarker loci in a nucleic acid sample collected from the patient, wherein the panel of biomarker loci comprises CpG dinucleotides in HP1BP3 loci and TTC9B loci, wherein the HP1BP3 loci is located at chr1:20986708-20986650 of human genome build hg 18 and the TTC9B loci is located at chr19:45416573 of human genome build hg 18;

b) analyzing the panel of biomarker loci using a classification algorithm to compare the DNA methylation levels including the HP1BP3 loci and the TTC9B loci of the patient to said HP1BP3 loci and said TTC9B loci of a patient not having or at risk of having PPD;

c) determining differential DNA methylation levels of the panel of biomarker loci relative to a corresponding panel of biomarker loci from a patient not having PPD or at risk of having PPD;

d) determining the patient has or is at risk of having PPD based on the analysis in c); and e) administering a PPD therapy regimen to the patient having or at risk of having PPD, wherein the PPD therapy regimen is administration of an antidepressant, thereby treating PPD in the patient.

2. The method of claim 1, wherein relative methylation levels of promoter regions of HP1BP3 and TTC9B are analyzed.

3. The method of claim 1, wherein the sample is collected from the patient in a first, second or third trimester of pregnancy.

4. The method of claim 1, wherein DNA methylation levels are determined by sodium bisulfite pyrosequencing, Methylation-sensitive Single Nucleotide Primer Extension (Ms-SNuPE) reaction, methylation-specific PCR or microarray analysis.

5. The method of claim 1, wherein the HP1BP3 loci comprises CpG dinucleotides located within the minus strand of chr1:20986708-20986650 of human genome build hg 18.

6. The method of claim 5, wherein the DNA methylation levels of HP1BP3 loci are analyzed using a primer comprising any of SEQ ID NOs: 8-12.

7. The method of claim 1, wherein the TTC9B loci comprises CpG dinucleotides located within the plus strand of chr19:45416573 of human genome build hg 18.

8. The method of claim 7, wherein the DNA methylation levels of TTC9B loci are analyzed using a primer comprising any of SEQ ID NOs: 13-17.

9. The method of claim 1, wherein the panel of biomarker loci further comprises CpG dinucleotides in PABPCIL loci, and wherein the PABPCIL loci comprises CpG dinucleotides located within the region of chr20:42971786-42971857 of human genome build hg 18.

10. The method of claim 9, wherein the PABPCIL loci comprises CpG dinucleotides located within the plus strand of chr20:42971786-42971857 of human genome build hg 18.

11. The method of claim 10, wherein the DNA methylation levels of PABPCIL loci are analyzed using a primer comprising any of SEQ ID NOs: 1-7.

12. The method of claim 1, wherein the panel of biomarker loci further comprises CpG dinucleotides in OXTR loci, and wherein the OXTR loci comprises CpG dinucleotides located within the region chr3:8785134-8785171 of human genome build hg 18.

13. The method of claim 12, wherein the OXTR loci comprises CpG dinucleotides located within the minus strand of chr3:8785134-8785171 of human genome build hg 18.

14. The method of claim 13, wherein the DNA methylation levels of OXTR loci are analyzed using a primer comprising any of SEQ ID NOS: 18-22.

15. The method of claim 1, wherein the classification algorithm uses one or more additive or interactive covariates to determine the patient has PPD.

16. The method of claim 1, wherein the classification algorithm uses stress, anxiety or sleep quality metrics from the patient across antenatal to postpartum periods as an additive or interactive covariate.

17. The method of claim 16, wherein the stress, anxiety and sleep quality metrics are taken from Pittsburgh Sleep Quality Index (PSQI) scale, Clinical Global Impression Scale (CGIS) scale, or Perceived Stress Scale (PSS) scale or a combination thereof.

18. A method for determining post-partum depression (PPD) therapy for a patient having or at risk of having PPD, comprising:

a) measuring DNA methylation levels of a panel of biomarker loci comprising HP1BP3 loci and TTC9B loci, and optionally PABPCIL loci and/or OXTR loci wherein the HP1BP3 loci is located at chr1:20986708-20986650 of human genome build hg 18, the TTC9B loci is located at chr19:45416573 of human genome build hg 18, the PABPCIL loci is located at chr20: 42971786-42971857 of human genome build hg 18, and the OXTR loci is located at chr3:8785134-8785171 of human genome build hg 18, and wherein the DNA methylation levels of HP1BP3 loci are measured by amplification using a primer comprising any of SEQ ID NOs: 8-12 and the DNA methylation levels of TTC9B loci are measured by amplification using a primer comprising any of SEQ ID NOs: 13-17; and b) using the relative DNA methylation levels of at least the HP1BP3 loci and the TTC9B loci of the patient compared to a control sample from a patient not having or at risk of having PPD, to determine the PPD therapy.

19. The method of claim 18, further comprising analyzing the panel of biomarker loci to identify change in DNA methylation levels, wherein identifying a change in DNA methylation levels is performed using a classification algorithm to determine PPD status using methylation levels from known samples.

20. The method of claim 19, wherein the classification algorithm uses one or more additive or interactive covariates to identify a change in DNA methylation levels to PPD indications.

21. The method of claim 19, wherein the classification algorithm uses stress, anxiety and sleep quality metrics from the patient across antenatal to postpartum periods as an additive or interactive covariate.

22. The method of claim 19, wherein the classification algorithm uses a total test score from a Pittsburgh Sleep Quality Index (PSQI) scale taken at the time of sample draw from the patient as an additive or interactive covariate.

23. The method of claim 22, wherein the classification algorithm uses a total test score from a Clinical Global Impression Scale (CGIS) scale taken at the time of sample draw from the patient as an additive or interactive covariate.

24. The method of claim 22, wherein the classification algorithm uses a total test score from a Perceived Stress Scale (PSS) scale taken at the time of sample draw from the patient as an additive or interactive covariate.

25. The method of claim 1, wherein the classification algorithm utilizes DNA methylation at HP1BP3 interacting with DNA methylation at OXTR or PABPCIL and utilizes DNA methylation at TTC9B as an additive covariate.

26. The method of claim 1, wherein the classification algorithm utilizes DNA methylation at HP1BP3 and TTC9B as additive covariates and the DNA methylation at OXTR or PABPCIL as an interacting component.

27. The method of claim 1, wherein the method further comprises collecting PPD phenotype or cell-type ratio from the patient, wherein the classification algorithm includes the PPD phenotype or cell-type ratio of the patient.

28. The method of claim 1, wherein the classification algorithm is a Kernel Method, SVM, a linear discriminant model, or a generalized linear model.

29. The method of claim 1, wherein the panel of biomarker loci further comprises PABPCIL loci and OXTR loci, wherein the HP1BP3 loci comprises CpG dinucleotides located within chr1:20986708-20986650 on the minus strand of human genome build hg 18, wherein the TTC9B loci comprises CpG dinucleotides within chr19:45416573 on the plus strand of human genome build hg 18, wherein the PABPCIL loci comprises CpG dinucleotides within chr20:42971786-42971857 on the plus strand of human genome build hg 18, and wherein the OXTR loci comprises CpG dinucleotides within chr3:8785134-8785171 on the minus strand of human genome build hg 18.

30. A method for determining an increased risk or likelihood of developing post-partum depression (PPD) in a human patient comprising:

a) estimating a ratio of monocytes to non-monocytes in a sample collected from the patient;

b) measuring DNA methylation levels of a panel of biomarker loci comprising HP1BP3 loci and TTC9B loci, in the sample collected from the patient by amplification using one or more primers comprising SEQ ID NOs: 8-17, wherein the HP1BP3 loci is located at chr1:20986708-20986650 of human genome build hg 18 and the TTC9B loci is located at chr19:45416573 of human genome build hg 18; and c) using a linear model that utilizes the DNA methylation level of HP1BP3, TTC9B and the ratio of monocytes: non-monocytes to determine that the patient is at increased risk or likelihood of developing PPD.

31. The method of claim 18, wherein the HP1BP3 loci comprises CpG dinucleotides located within a promoter region of HP1BP3, the TTC9B loci comprises CpG dinucleotides located within a promoter region of TTC9B, the PABPCIL loci comprise CpG dinucleotides located within the region chr20:42971786-42971857 on the positive strand of human genome build hg 18, and the OXTR loci comprises CpG dinucleotides located within the promoter region of OXTR.

* * * * *

SEQUENCE LISTING

<160> NUMBER OF SEQ ID NOS: 22

<210> SEQ ID NO 1
<211> LENGTH: 23
<212> TYPE: DNA
<213> ORGANISM: Artificial Sequence
<220> FEATURE:
<223> OTHER INFORMATION: PABPC1L_F_out

<400> SEQUENCE: 1
tttggtgtaa tggatgtgta atg 23

<210> SEQ ID NO 2
<211> LENGTH: 23
<212> TYPE: DNA
<213> ORGANISM: Artificial Sequence
<220> FEATURE:
<223> OTHER INFORMATION: PABPC1L_R_out

<400> SEQUENCE: 2
aaaccttcaa cctaacctta aac 23

<210> SEQ ID NO 3
<211> LENGTH: 29
<212> TYPE: DNA
<213> ORGANISM: Artificial Sequence
<220> FEATURE:
<223> OTHER INFORMATION: PABPC1L_F_in (biotin)

<400> SEQUENCE: 3
tatgagttag tattaagaaa ggttttagt 29

<210> SEQ ID NO 4
<211> LENGTH: 23
<212> TYPE: DNA
<213> ORGANISM: Artificial Sequence
<220> FEATURE:
<223> OTHER INFORMATION: PABPC1L_R_in

<400> SEQUENCE: 4
aaactctcaa aacccccaac tct 23

<210> SEQ ID NO 5
<211> LENGTH: 23
<212> TYPE: DNA
<213> ORGANISM: Artificial Sequence
<220> FEATURE:
<223> OTHER INFORMATION: PABPC1L_Pyro1

<400> SEQUENCE: 5
caaaaaacct aatccaatcc cac 23

<210> SEQ ID NO 6
<211> LENGTH: 25
<212> TYPE: DNA
<213> ORGANISM: Artificial Sequence
<220> FEATURE:
<223> OTHER INFORMATION: PABPC1L_Pyro2

<400> SEQUENCE: 6
aaacaaataa tcatctttct aaacc 25

<210> SEQ ID NO 7
<211> LENGTH: 31
<212> TYPE: DNA
<213> ORGANISM: Artificial Sequence
<220> FEATURE:
<223> OTHER INFORMATION: PABPC1L_Pyro3

<400> SEQUENCE: 7
ctcctaacaa aaataaaaaa aaacccaaac c 31

<210> SEQ ID NO 8
<211> LENGTH: 30
<212> TYPE: DNA
<213> ORGANISM: Artificial Sequence
<220> FEATURE:
<223> OTHER INFORMATION: HP1BP3_F_out

<400> SEQUENCE: 8 attttttaa attagttttg aagagttgta 30

<210> SEQ ID NO 9
<211> LENGTH: 26
<212> TYPE: DNA
<213> ORGANISM: Artificial Sequence
<220> FEATURE:
<223> OTHER INFORMATION: HP1BP3_R_out

<400> SEQUENCE: 9
cctaaaaaaa aatccaccaa aaaaac 26

<210> SEQ ID NO 10
<211> LENGTH: 26
<212> TYPE: DNA
<213> ORGANISM: Artificial Sequence
<220> FEATURE:
<223> OTHER INFORMATION: HP1BP3_F_in

<400> SEQUENCE: 10
tttttttgta tgtgaggatt agggag 26

<210> SEQ ID NO 11
<211> LENGTH: 26
<212> TYPE: DNA
<213> ORGANISM: Artificial Sequence
<220> FEATURE:
<223> OTHER INFORMATION: HP1BP3_R_in (biotin)

<400> SEQUENCE: 11
caatcccttc tcttaactaa atttcc 26

<210> SEQ ID NO 12
<211> LENGTH: 26
<212> TYPE: DNA
<213> ORGANISM: Artificial Sequence
<220> FEATURE:
<223> OTHER INFORMATION: HP1BP3_Pyro1

<400> SEQUENCE: 12
ttaaaaaaag gtttgttttt gagttg 26

<210> SEQ ID NO 13
<211> LENGTH: 21
<212> TYPE: DNA
<213> ORGANISM: Artificial Sequence
<220> FEATURE:
<223> OTHER INFORMATION: TTC9B_F_out

<400> SEQUENCE: 13
gggggaaaga gtaggaagat a 21

<210> SEQ ID NO 14
<211> LENGTH: 25
<212> TYPE: DNA
<213> ORGANISM: Artificial Sequence
<220> FEATURE:
<223> OTHER INFORMATION: TTC9B_R_out

<400> SEQUENCE: 14
aaactaatct caaacttcta acctc 25

<210> SEQ ID NO 15
<211> LENGTH: 28
<212> TYPE: DNA
<213> ORGANISM: Artificial Sequence
<220> FEATURE:
<223> OTHER INFORMATION: TTC9B_F_in (biotin)

<400> SEQUENCE: 15
gaatgagaat ataggatttg gatttaag 28

<210> SEQ ID NO 16
<211> LENGTH: 34
<212> TYPE: DNA
<213> ORGANISM: Artificial Sequence
<220> FEATURE:
<223> OTHER INFORMATION: TTC9B_R_in

<400> SEQUENCE: 16
cctaaaaata atattattat accatattac taat 34

<210> SEQ ID NO 17
<211> LENGTH: 24
<212> TYPE: DNA
<213> ORGANISM: Artificial Sequence
<220> FEATURE:
<223> OTHER INFORMATION: TTC9B_Pyro1

<400> SEQUENCE: 17
tacaaaattc caaataattt aaac 24

<210> SEQ ID NO 18
<211> LENGTH: 23
<212> TYPE: DNA
<213> ORGANISM: Artificial Sequence
<220> FEATURE:
<223> OTHER INFORMATION: OXTR_F_out

<400> SEQUENCE: 18
gggaggtgat ttggttttag att 23

<210> SEQ ID NO 19
<211> LENGTH: 23
<212> TYPE: DNA
<213> ORGANISM: Artificial Sequence
<220> FEATURE:
<223> OTHER INFORMATION: OXTR_R_out

<400> SEQUENCE: 19
aaactccact cctaaaaact cca 23

<210> SEQ ID NO 20
<211> LENGTH: 25
<212> TYPE: DNA
<213> ORGANISM: Artificial Sequence
<220> FEATURE:
<223> OTHER INFORMATION: OXTR_F_in

```
<400> SEQUENCE: 20

tatttgtagt ggtttagagg aggta                                            25


<210> SEQ ID NO 21
<211> LENGTH: 25
<212> TYPE: DNA
<213> ORGANISM: Artificial Sequence
<220> FEATURE:
<223> OTHER INFORMATION: OXTR_R_in (biotin)

<400> SEQUENCE: 21

tactaaatcc accctaaaac aaacc                                            25


<210> SEQ ID NO 22
<211> LENGTH: 29
<212> TYPE: DNA
<213> ORGANISM: Artificial Sequence
<220> FEATURE:
<223> OTHER INFORMATION: OXTR_Pyro1

<400> SEQUENCE: 22

gagttgggtt tttgggaatg ggataagta                                        29
```